US011129756B2

(12) United States Patent
Schneider et al.

(10) Patent No.: US 11,129,756 B2
(45) Date of Patent: Sep. 28, 2021

(54) APPARATUSES AND METHODS FOR MAKING ABSORBENT ARTICLES

(71) Applicant: The Procter & Gamble Company, Cincinnati, OH (US)

(72) Inventors: Uwe Schneider, Cincinnati, OH (US); Hui Yang, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/691,753

(22) Filed: Nov. 22, 2019

(65) Prior Publication Data

US 2020/0085642 A1    Mar. 19, 2020

Related U.S. Application Data

(63) Continuation of application No. 14/967,447, filed on Dec. 14, 2015, now Pat. No. 10,517,773.

(Continued)

(51) Int. Cl.
*A61F 13/49* (2006.01)
*A61F 13/15* (2006.01)
(Continued)

(52) U.S. Cl.
CPC .. *A61F 13/49009* (2013.01); *A61F 13/15203* (2013.01); *A61F 13/15723* (2013.01);
(Continued)

(58) Field of Classification Search
CPC .......... A61F 13/15203; A61F 13/51496; A61F 2013/15243; A61F 2013/8497;
(Continued)

(56) References Cited

U.S. PATENT DOCUMENTS 3,860,003 A    1/1975   Buell
4,610,678 A    9/1986   Weisman et al.
(Continued)

FOREIGN PATENT DOCUMENTS

EP        1 712 212 A2    10/2006
JP        2008183332       8/2008
(Continued)

OTHER PUBLICATIONS

All Office Actions, U.S. Appl. No. 14/967,447.
(Continued)

*Primary Examiner* — Vishal I Patel
(74) *Attorney, Agent, or Firm* — Charles R. Matson

(57) ABSTRACT

The present disclosure relates to printing graphics onto advancing substrates in diaper converting lines, wherein first graphics having relatively low print resolutions and second graphics having relatively high print resolutions may be both printed onto advancing substrates. During the assembly process, localized speed variances may be imparted to the advancing substrates to achieve the different print resolutions. In some configurations, first graphics with relatively low print resolutions may be printed onto the substrate while advancing at relatively high speeds, and second graphics with relatively high print resolutions may be printed onto portions of the substrate that have been temporarily stopped or slowed to relatively slow speed. The printed substrates may then be incorporated into assembled diapers so as place the graphics in desired positions on the diapers.

11 Claims, 25 Drawing Sheets

Related U.S. Application Data

(60) Provisional application No. 62/093,438, filed on Dec. 18, 2014.

(51) Int. Cl.
*A61F 13/514* (2006.01)
*A61F 13/84* (2006.01)

(52) U.S. Cl.
CPC .. *A61F 13/15731* (2013.01); *A61F 13/15747* (2013.01); *A61F 13/15804* (2013.01); *A61F 13/51496* (2013.01); *A61F 2013/15243* (2013.01); *A61F 2013/8497* (2013.01)

(58) Field of Classification Search
CPC .......... A61F 13/15804; A61F 13/15731; A61F 13/15723; A61F 13/15747; A61F 13/49009
See application file for complete search history.

(56) References Cited

U.S. PATENT DOCUMENTS

| | | |
|---|---|---|
| 4,673,402 A | 6/1987 | Weisman et al. |
| 4,695,278 A | 9/1987 | Lawson |
| 4,704,115 A | 11/1987 | Buell |
| 4,720,321 A | 6/1988 | Smith |
| 4,795,454 A | 1/1989 | Dragoo |
| 4,834,735 A | 5/1989 | Alemany et al. |
| 4,888,231 A | 12/1989 | Angstadt |
| 4,909,803 A | 3/1990 | Aziz et al. |
| 5,373,761 A | 12/1994 | Brining |
| 5,562,646 A | 10/1996 | Goldman et al. |
| 5,599,335 A | 2/1997 | Goldman et al. |
| 5,628,097 A | 5/1997 | Benson et al. |
| 5,669,894 A | 9/1997 | Goldman et al. |
| 5,693,165 A | 12/1997 | Schmitz |
| 5,916,661 A | 6/1999 | Benson et al. |
| 6,107,539 A | 8/2000 | Palumbo et al. |
| 6,349,867 B1 | 2/2002 | Fernfors |
| 6,545,197 B1 | 4/2003 | Muller et al. |
| 6,596,108 B2 | 7/2003 | McCabe |
| 6,620,276 B1 | 9/2003 | Kuntze et al. |
| 6,790,798 B1 | 9/2004 | Suzuki et al. |
| 7,569,039 B2 | 8/2009 | Matsuda et al. |
| 7,587,966 B2 | 9/2009 | Nakakado et al. |
| 7,896,858 B2 | 3/2011 | Trennepohl et al. |
| D657,454 S | 4/2012 | Gehrke et al. |
| 8,377,249 B2 | 2/2013 | Gill |
| 8,440,043 B1 | 5/2013 | Schneider et al. |
| 8,585,666 B2 | 11/2013 | Weisman et al. |
| 8,691,041 B2 | 4/2014 | Oetjen |
| 8,776,683 B2 | 7/2014 | Schneider |
| 2003/0066594 A1 | 4/2003 | Malakouti et al. |
| 2003/0073966 A1 | 4/2003 | Sosalla et al. |
| 2003/0158532 A1 | 8/2003 | Magee et al. |
| 2004/0097895 A1 | 5/2004 | Busam et al. |
| 2004/0108043 A1 | 6/2004 | Otsubo |
| 2004/0158212 A1 | 8/2004 | Ponomarenko et al. |
| 2004/0243083 A1 | 12/2004 | Matauda et al. |
| 2005/0107764 A1 | 5/2005 | Matsuda et al. |
| 2005/0217791 A1* | 10/2005 | Costello ................. B41J 3/546 156/277 |
| 2005/0267431 A1 | 12/2005 | Sasaki et al. |
| 2006/0108054 A1 | 5/2006 | Ukegawa |
| 2008/0091162 A1 | 4/2008 | Maldonado et al. |
| 2008/0132872 A1 | 6/2008 | Trennepohl et al. |
| 2009/0030389 A1 | 1/2009 | Ashton et al. |
| 2009/0312730 A1 | 12/2009 | LaVon et al. |
| 2010/0168703 A1 | 7/2010 | Tange et al. |
| 2011/0088828 A1 | 4/2011 | Misek et al. |
| 2011/0094661 A1 | 4/2011 | Thorson |
| 2011/0094669 A1 | 4/2011 | Oetjen |
| 2011/0209334 A1 | 9/2011 | Trennepohl et al. |
| 2012/0029454 A1 | 2/2012 | Li et al. |
| 2012/0061015 A1 | 3/2012 | LaVon et al. |
| 2012/0061016 A1 | 3/2012 | LaVon et al. |
| 2013/0255861 A1 | 10/2013 | Schneider |
| 2013/0255862 A1* | 10/2013 | Schneider ......... A61F 13/15593 156/161 |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0261589 A1 | 10/2013 | Fujkawa et al. |
| 2013/0270065 A1 | 10/2013 | Papsdorf et al. |
| 2013/0270066 A1 | 10/2013 | Papsdorf et al. |
| 2013/0270067 A1 | 10/2013 | Papsdorf et al. |
| 2013/0270069 A1 | 10/2013 | Papsdorf et al. |
| 2013/0310798 A1 | 11/2013 | Glahn et al. |
| 2014/0005020 A1 | 1/2014 | LaVon et al. |
| 2014/0174648 A1 | 6/2014 | Oetjen |
| 2014/0174651 A1 | 6/2014 | Oetjen |
| 2015/0148768 A1 | 5/2015 | Fukasawa et al. |
| 2016/0175161 A1 | 6/2016 | Zink, II et al. |
| 2016/0175165 A1 | 6/2016 | Schneider et al. |
| 2016/0175166 A1 | 6/2016 | Zink, II et al. |
| 2016/0175167 A1 | 6/2016 | Sauer et al. |
| 2016/0175168 A1 | 6/2016 | Zink, II et al. |
| 2017/0172809 A1 | 6/2017 | Wagner et al. |
| 2017/0172814 A1 | 6/2017 | Wagner et al. |
| 2017/0172815 A1 | 6/2017 | Wagner et al. |
| 2017/0172816 A1 | 6/2017 | Wagner et al. |

FOREIGN PATENT DOCUMENTS

| | | |
|---|---|---|
| WO | WO 2004105664 | 12/2004 |
| WO | WO 2015/134459 A1 | 9/2005 |
| WO | WO 2008/070131 A2 | 6/2008 |
| WO | WO 2011042513 | 4/2011 |
| WO | WO 2011045684 | 4/2011 |
| WO | WO 2012/054662 A1 | 4/2012 |
| WO | WO 2016/100246 A1 | 6/2016 |
| WO | WO 2016/100247 A1 | 6/2016 |
| WO | WO 2016/100250 A1 | 6/2016 |
| WO | WO 2016/100501 A1 | 6/2016 |

OTHER PUBLICATIONS

All Office Actions, U.S. Appl. No. 14/967,421.
All Office Actions, U.S. Appl. No. 14/967,430.
All Office Actions, U.S. Appl. No. 14/967,434.
All Office Actions, U.S. Appl. No. 14/967,440.
All Office Actions, U.S. Appl. No. 15/378,129.
All Office Actions, U.S. Appl. No. 15/378,149.
All Office Actions, U.S. Appl. No. 15/378,164.
All Office Actions, U.S. Appl. No. 15/378,195.
PCT International Search Report dated Mar. 30, 2016, 11 pages.
All Office Actions, U.S. Appl. No. 17/237,097.
U.S. Unpublished Patent Application U.S. Appl. No. 17/237,097, filed Apr. 22, 2021, to Sauer Linda Ann et al.

* cited by examiner

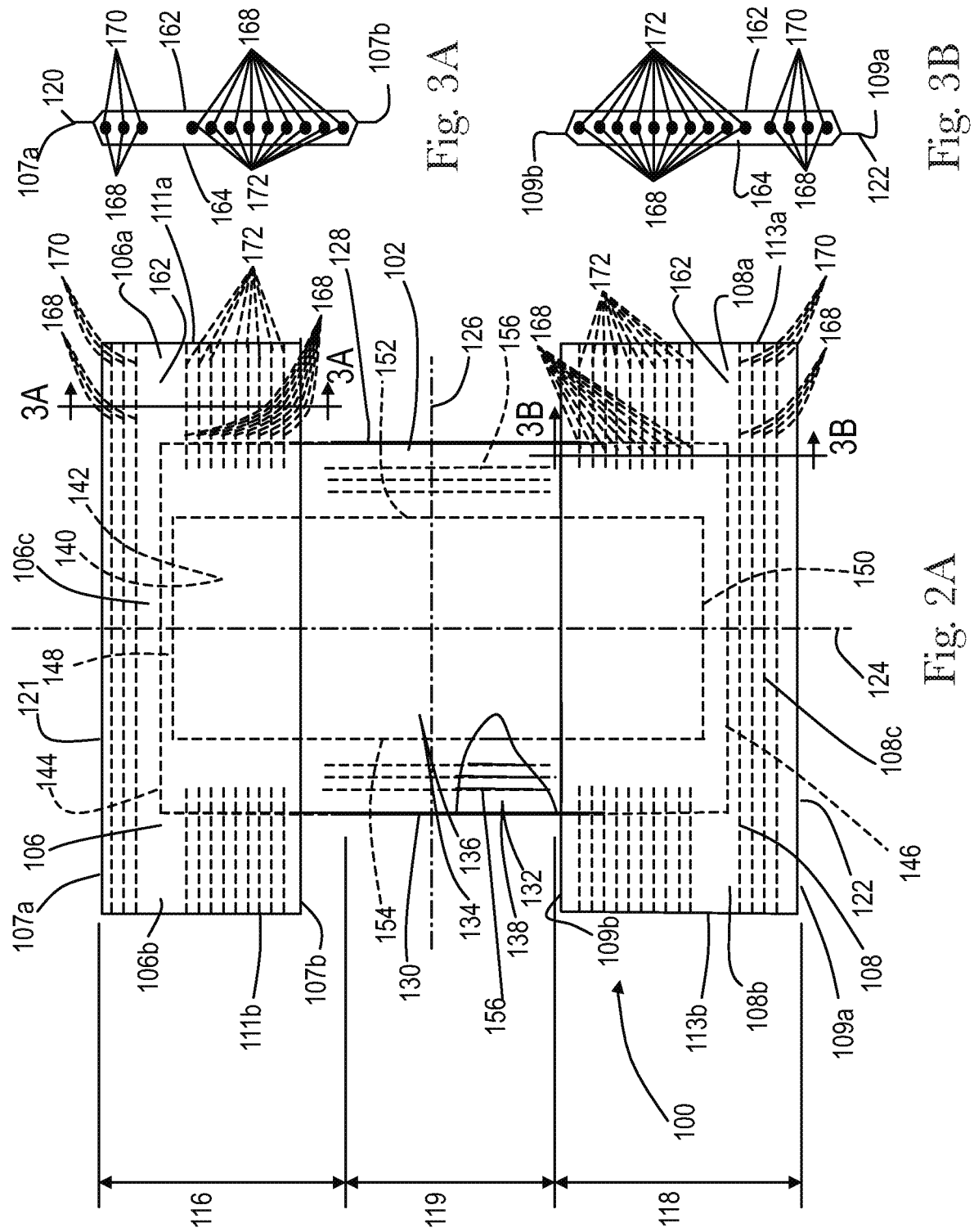

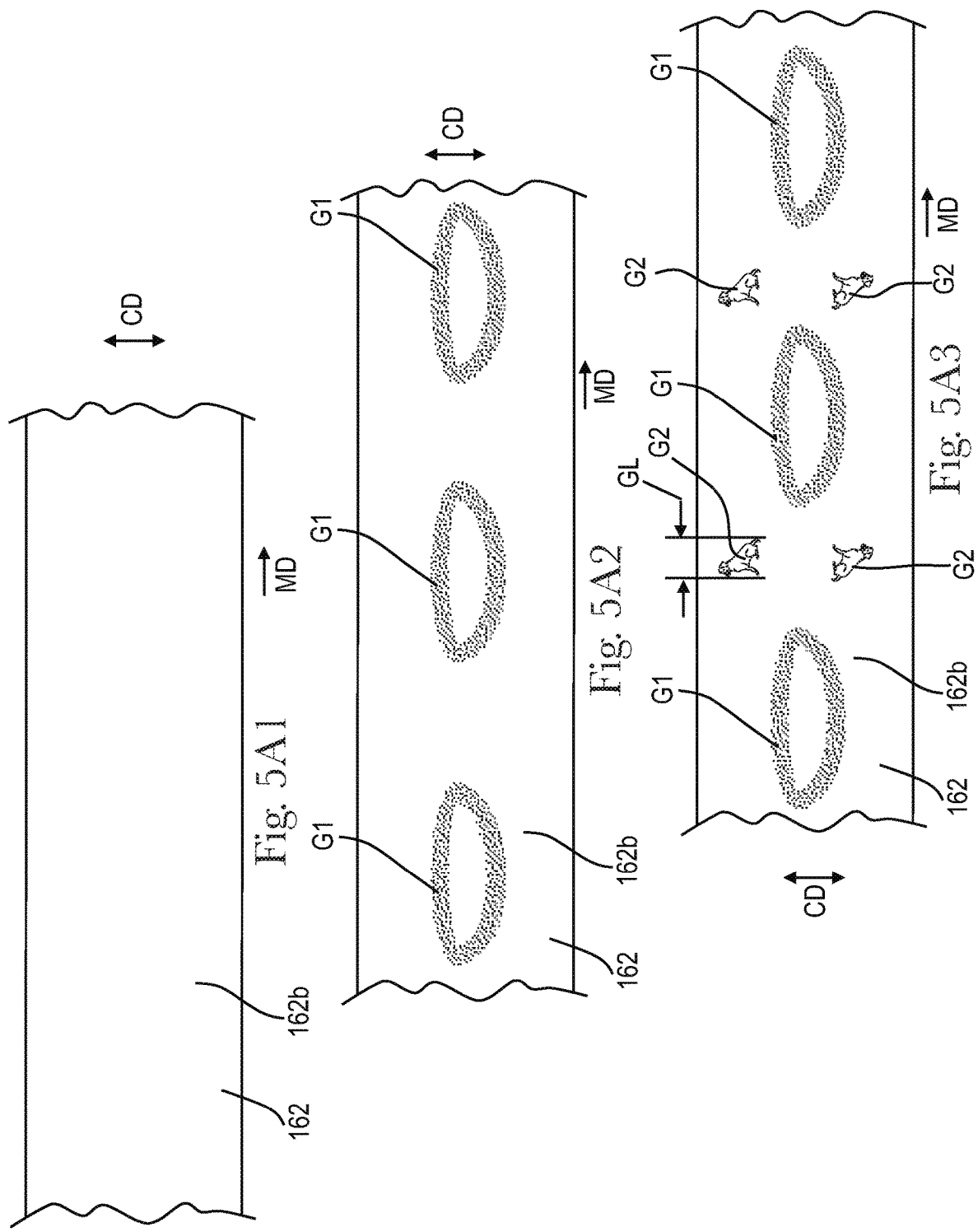

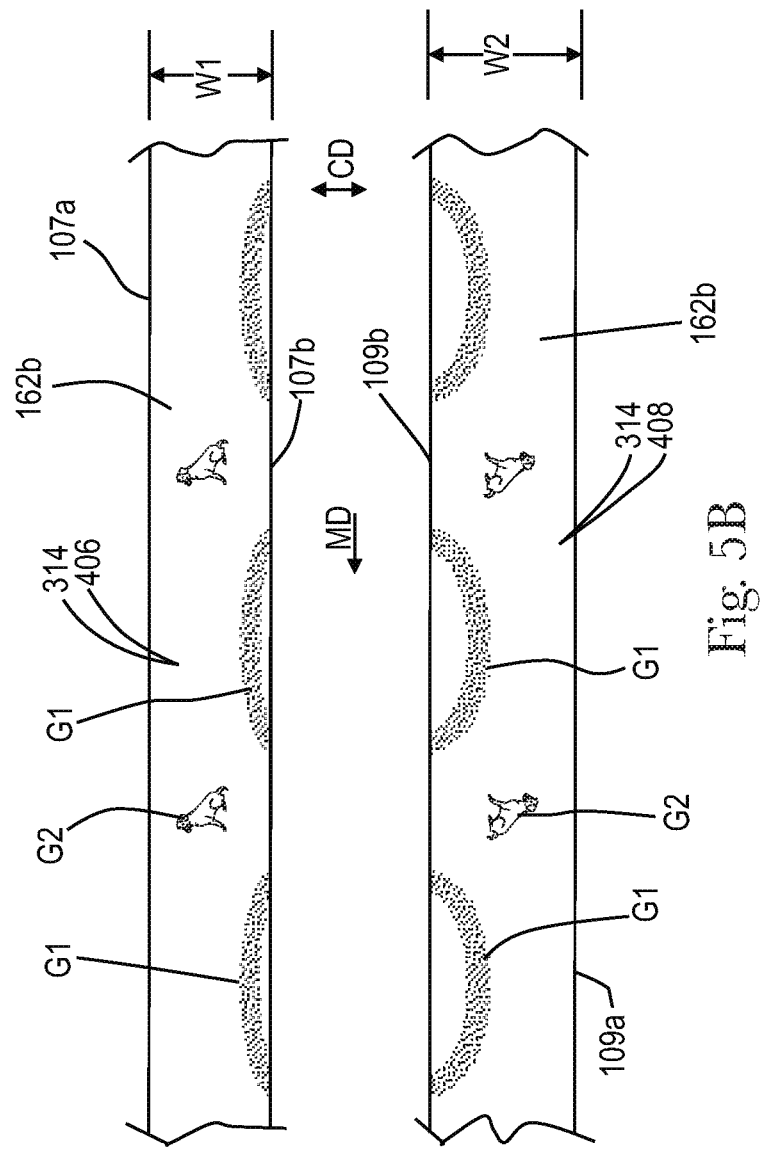

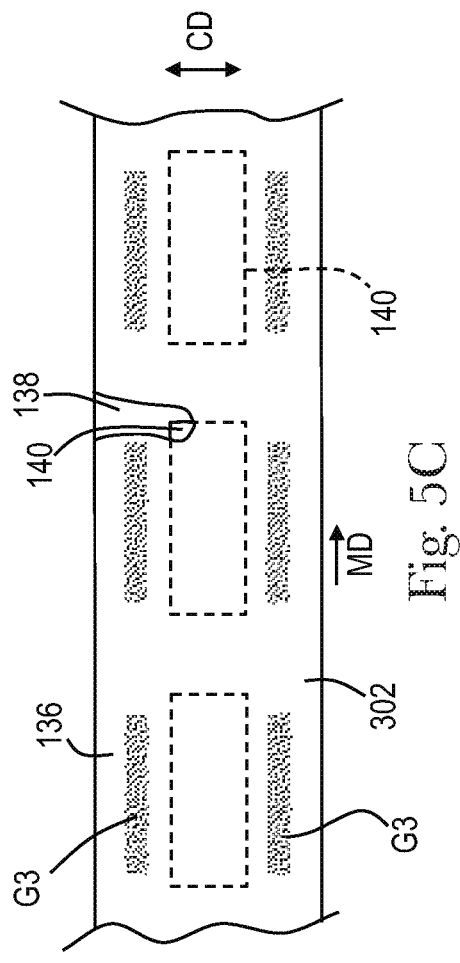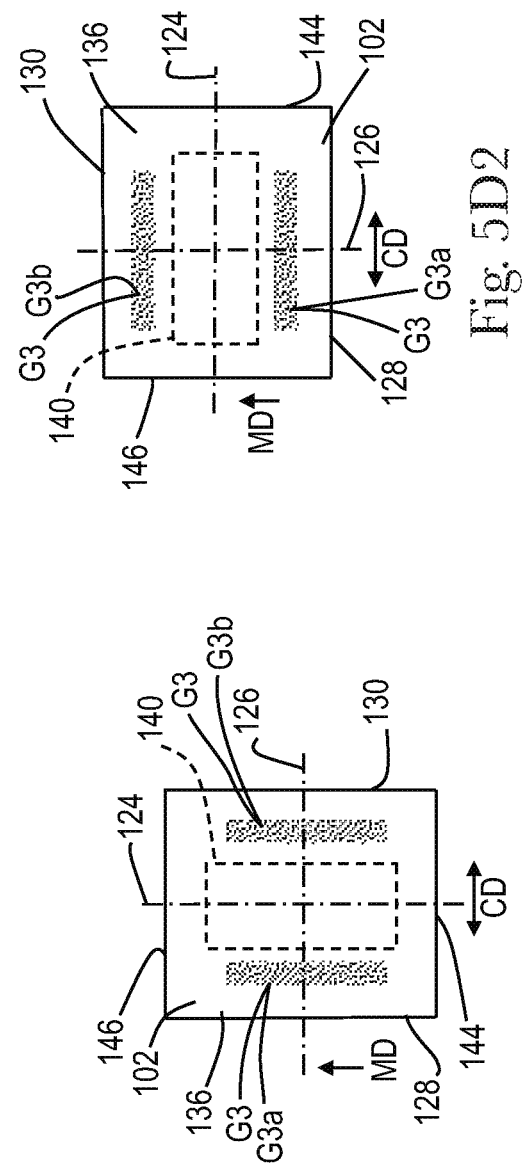

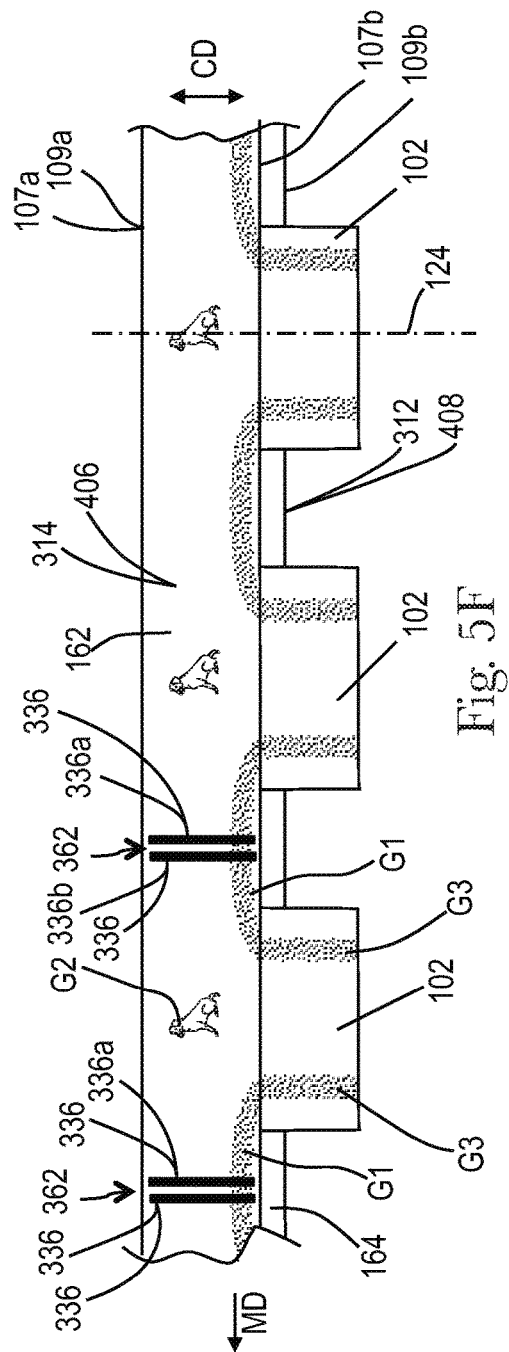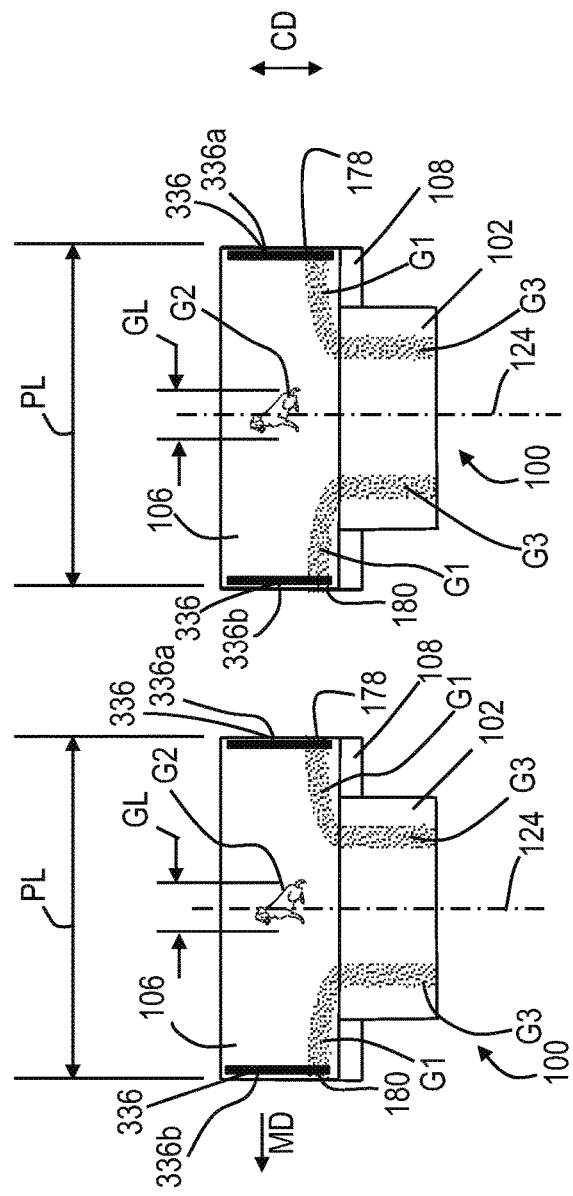

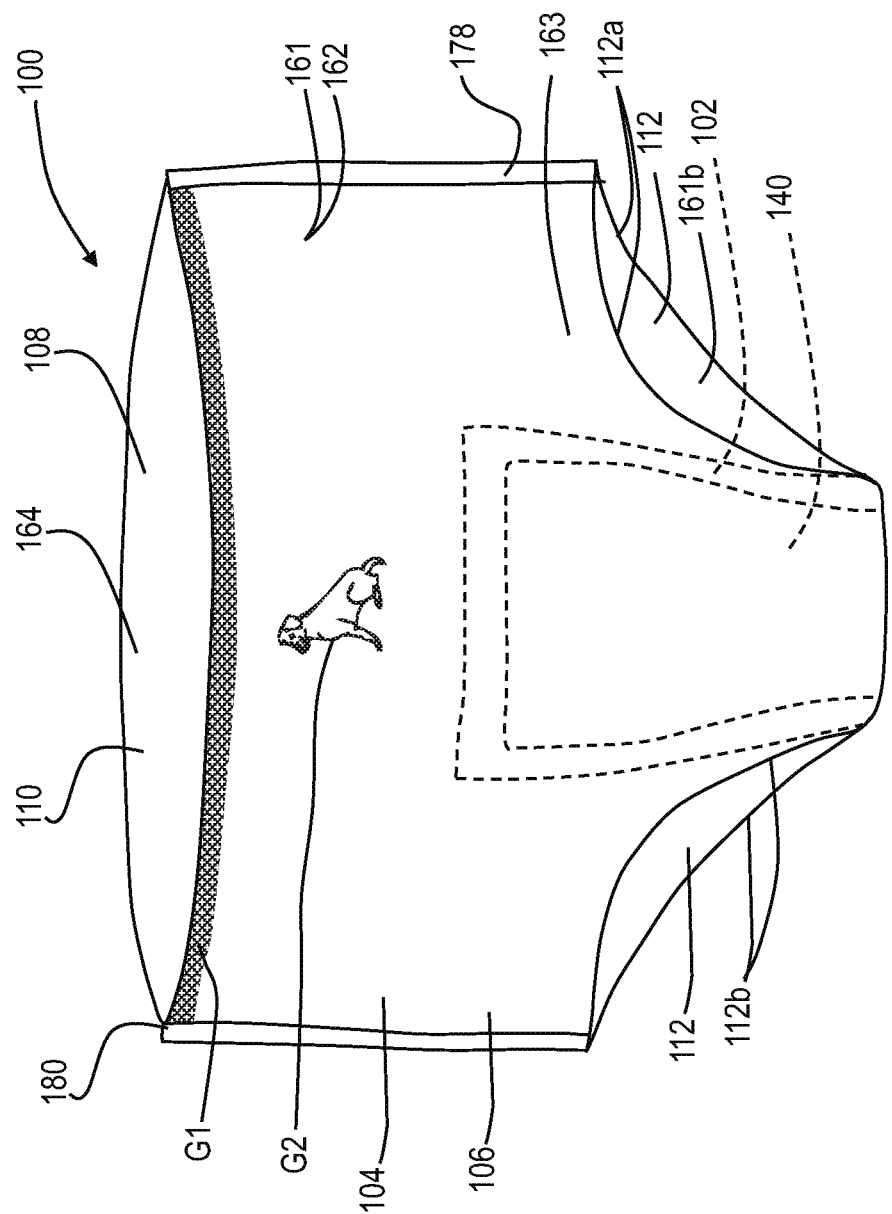

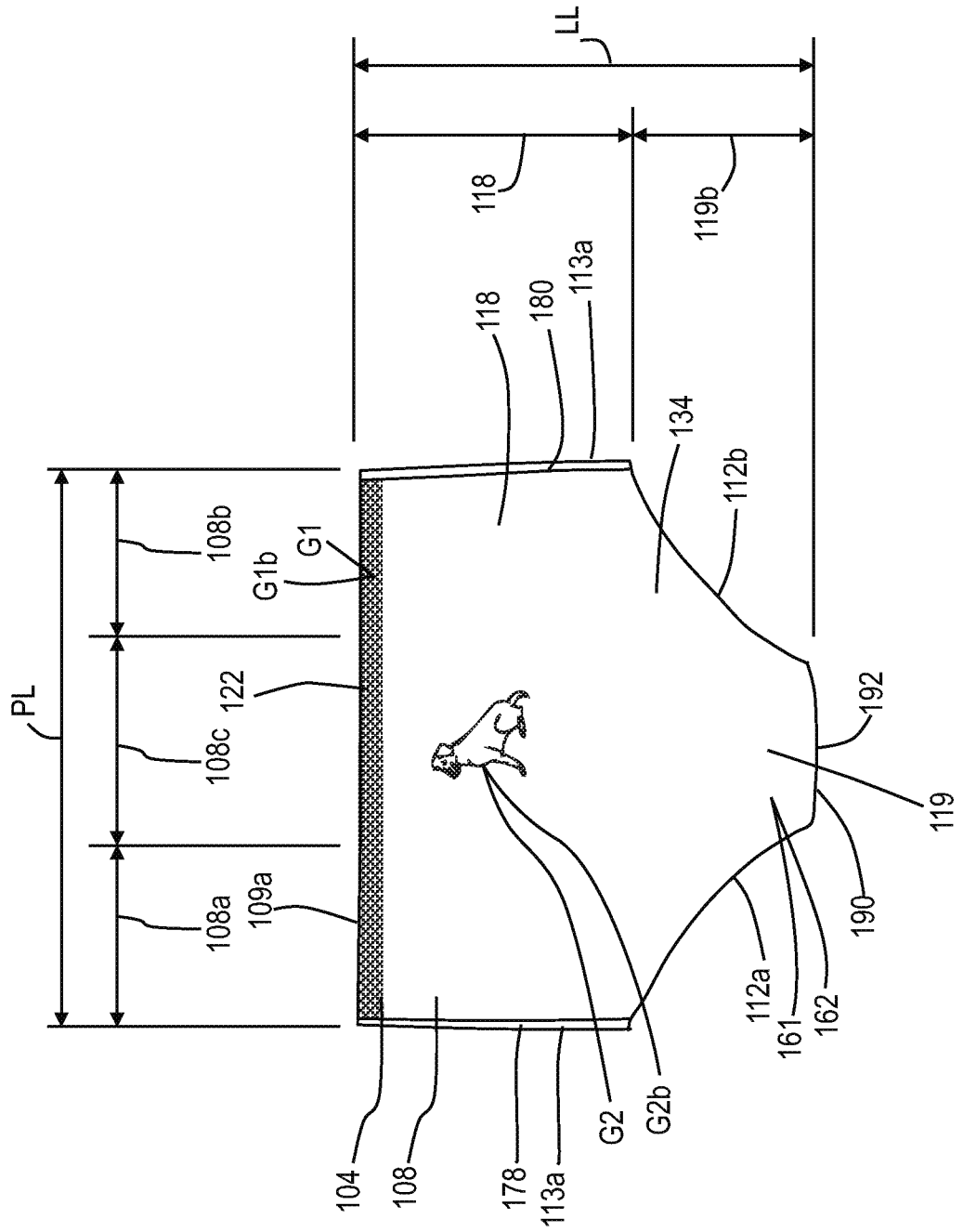

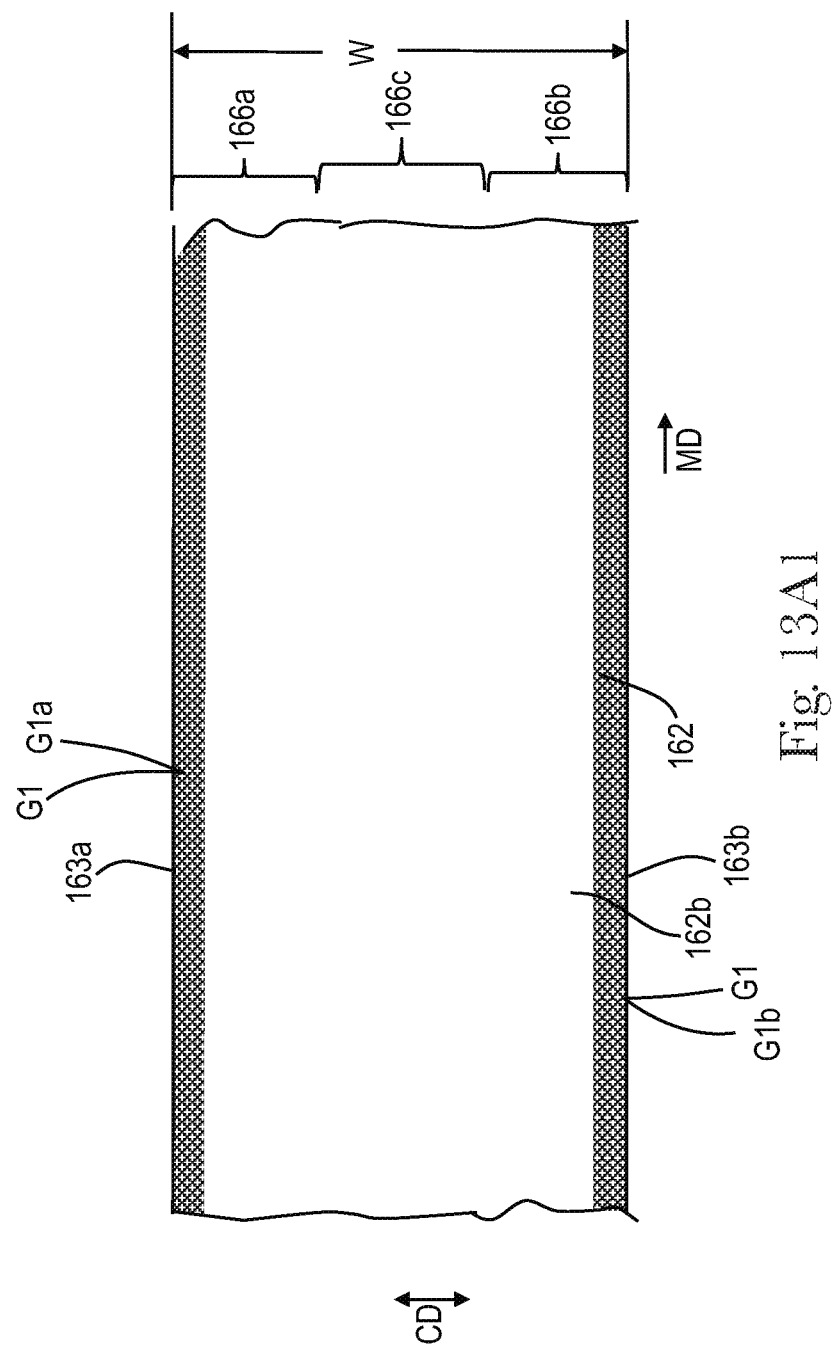
Fig. 13A1

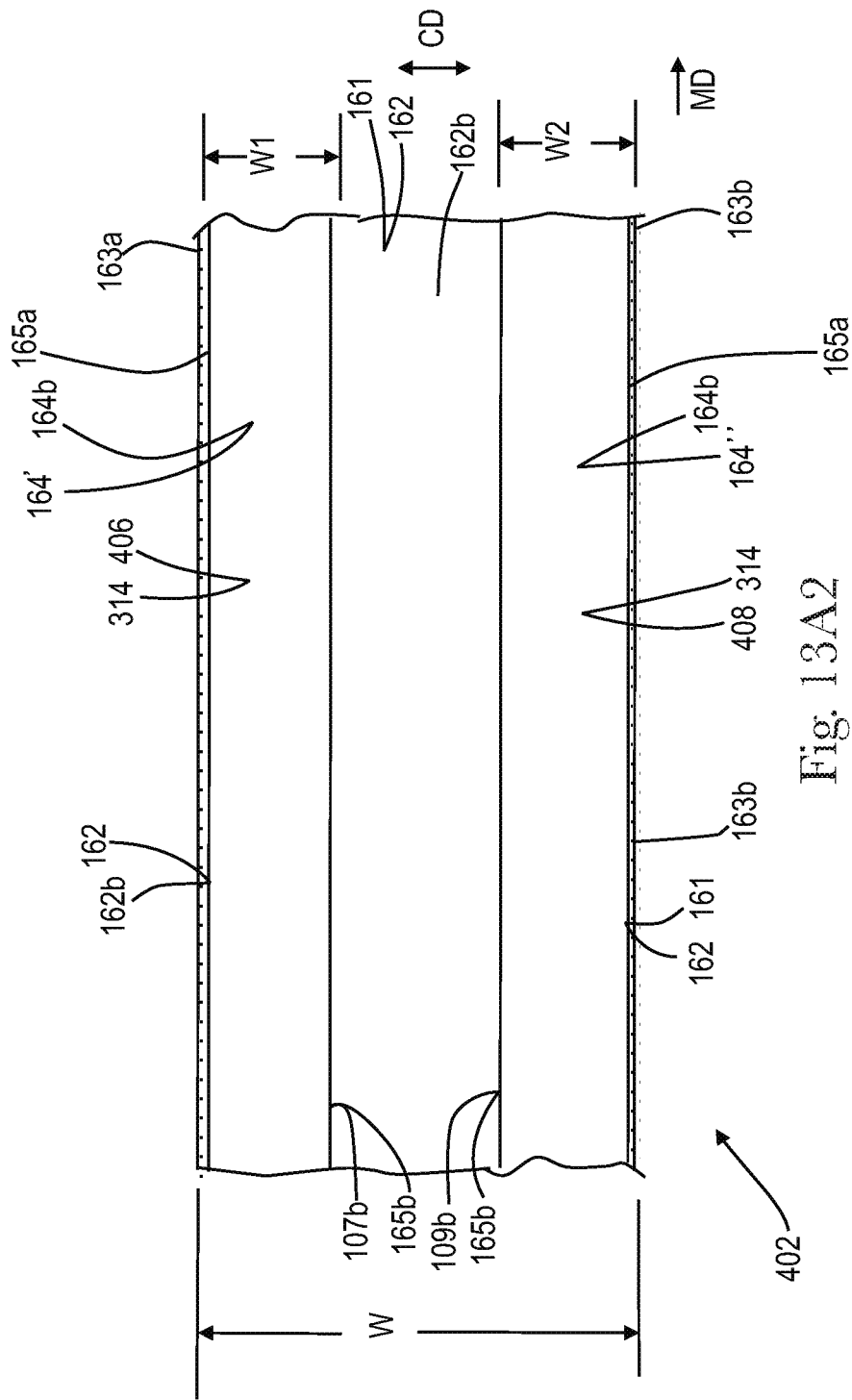
Fig. 13A2

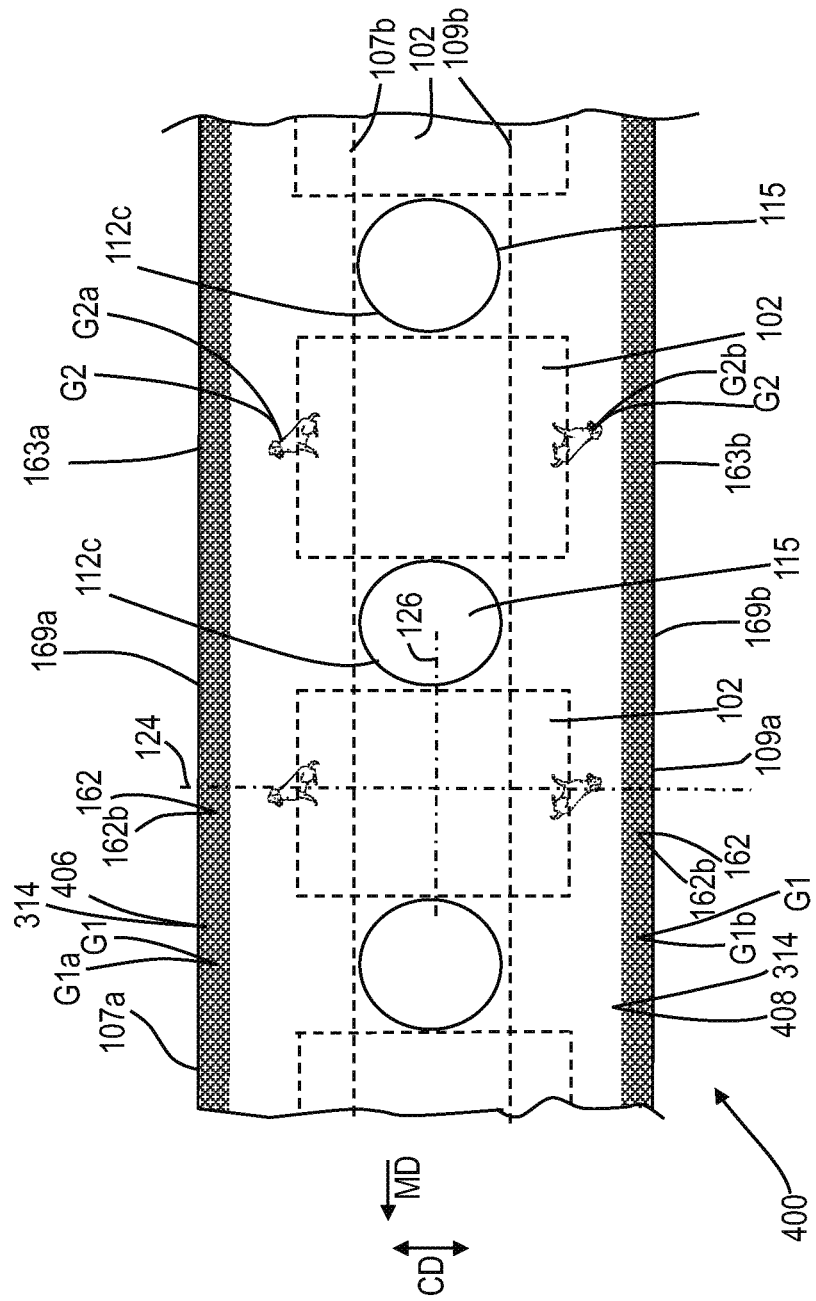
Fig. 13E1

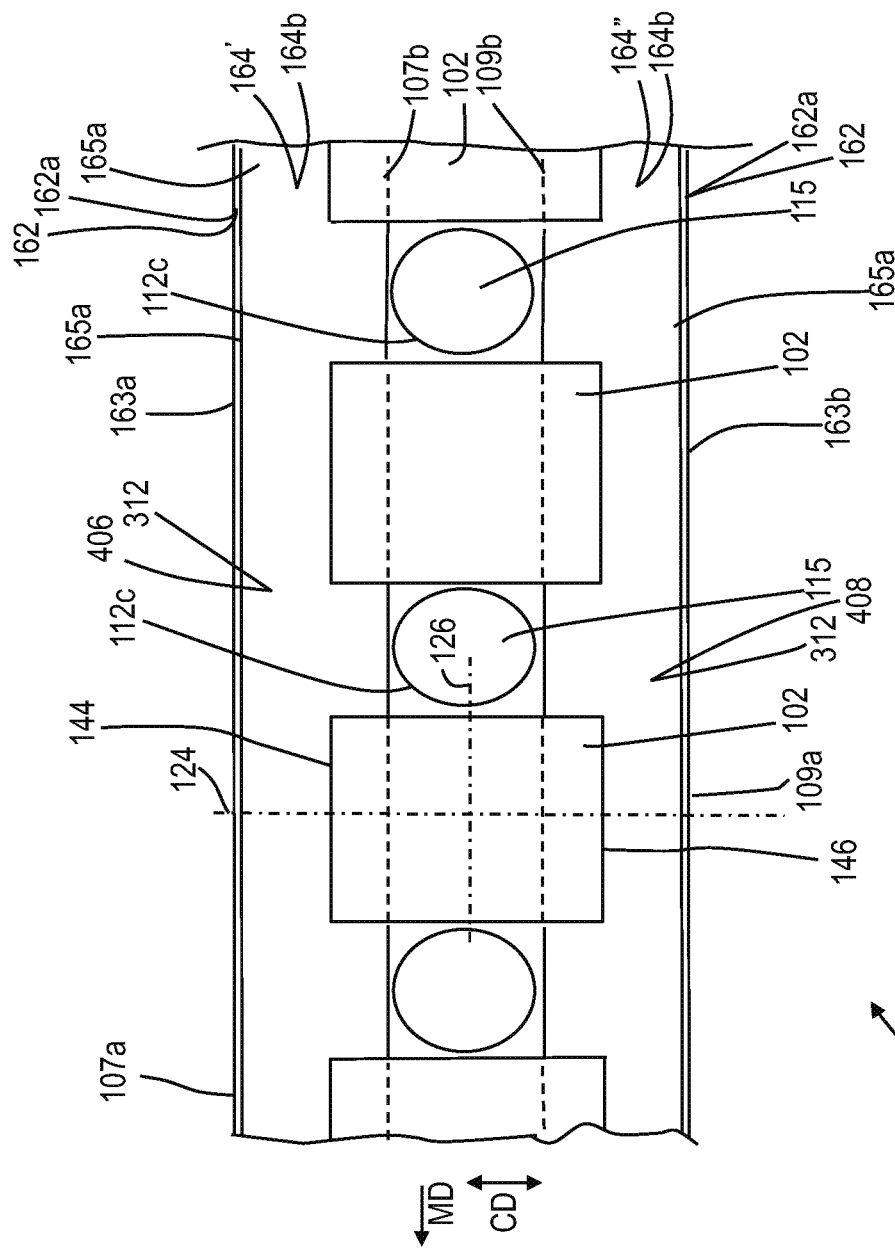
Fig. 13E2

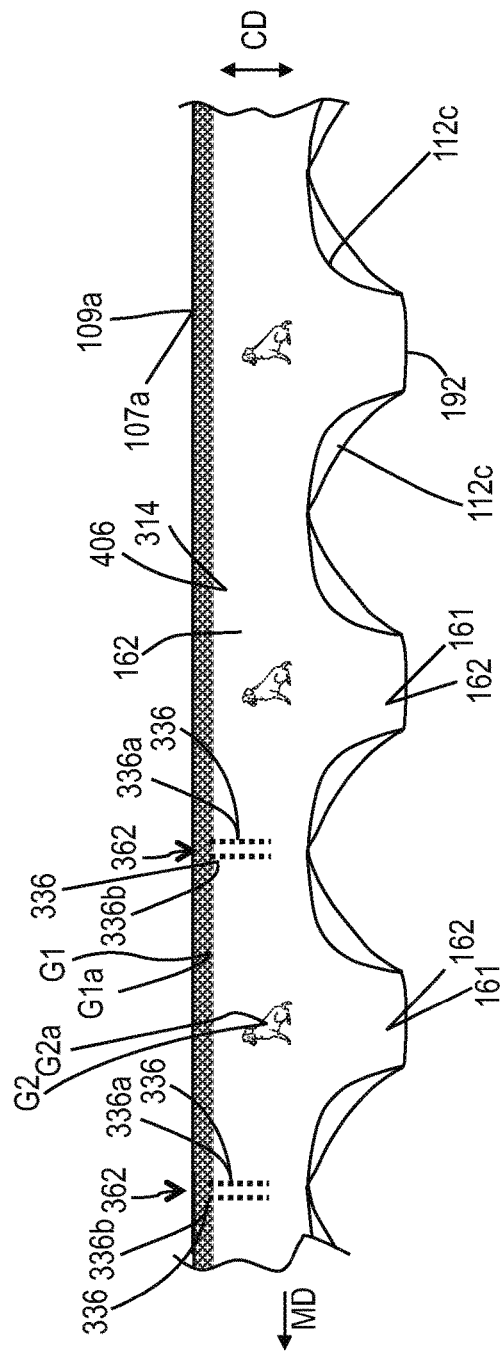
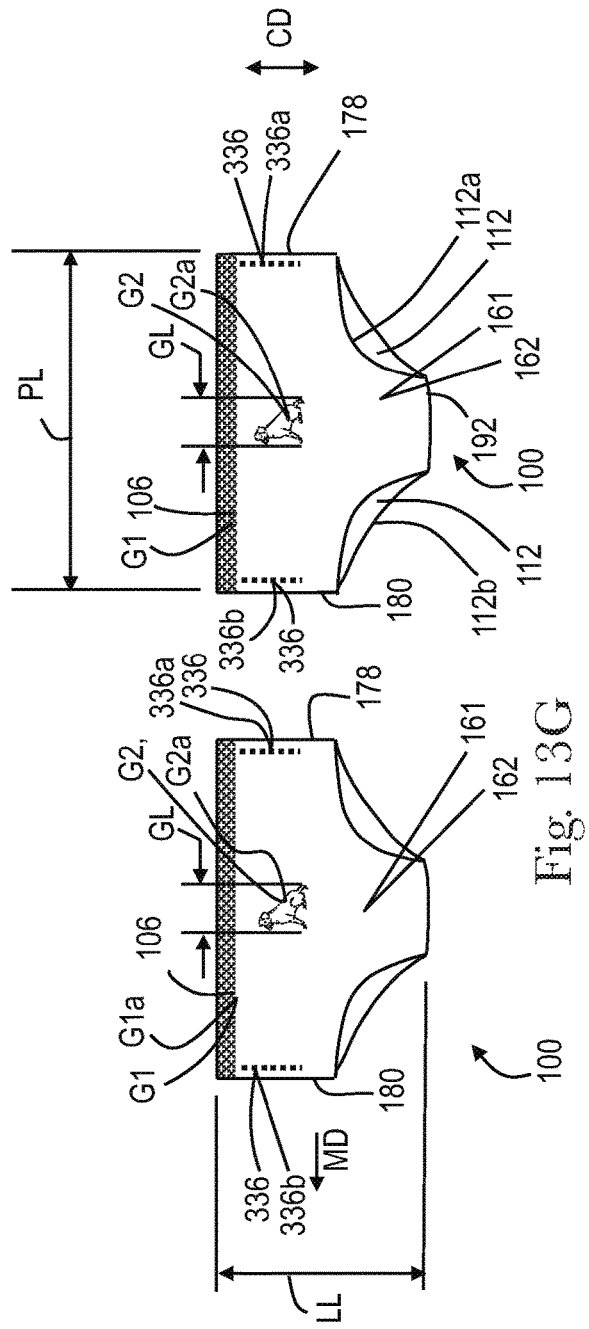

APPARATUSES AND METHODS FOR MAKING ABSORBENT ARTICLES

CROSS REFERENCE TO RELATED APPLICATIONS

This application is a continuation of U.S. application Ser. No. 14/967,447, filed on Dec. 14, 2015, which claims the benefit of U.S. Provisional Application No. 62/093,438 filed on Dec. 18, 2014, both of which are incorporated by reference herein.

FIELD OF THE INVENTION

The present disclosure relates to methods for manufacturing absorbent articles, and more particularly, to apparatuses and methods of inkjet printing graphics having different print resolutions by imparting localized speed variances to advancing substrates in diaper converting lines.

BACKGROUND OF THE INVENTION

Along an assembly line, diapers and various types of other disposable absorbent articles may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. In some processes, graphics are printed on individual components and/or continuous webs of material used to assemble the absorbent articles.

Some consumers may prefer purchasing absorbent articles, such as diapers, having a number of different graphic designs printed thereon and provided in a single package. Further, some consumers may prefer purchasing diapers having graphics printed thereon with relatively high print resolutions. Various methods and apparatuses can be used to print different graphics on an advancing web of material used in the manufacture of absorbent articles. However, such methods and apparatuses may provide for limited numbers of different printed graphics, graphics with relatively low quality print, and/or require relatively low print and/or manufacture speeds. In addition, such methods and apparatuses may also require relatively expensive processes and equipment and may not be very flexible in allowing a user to change the type of graphics to be printed.

Thus, in some circumstances it may be desirable to utilize ink jet or some other type of non-contact printing to print graphics, because of the relatively high degree of flexibility and relative ease to change the graphics that are being printed. However, the relatively slow speeds associated with such non-contact printing techniques may create challenges in printing graphics with relatively high print resolutions, particularly when such non-contact printing techniques are incorporated into absorbent article assembly processes operating at relatively high speed production rates. Consequently, there remains a demand to use non-contact printing techniques in diaper manufacturing processes to print graphics having relatively high print resolutions that maintain desired aesthetic benefits on assembled diapers without sacrificing relatively high manufacturing speeds.

SUMMARY OF THE INVENTION

The present disclosure relates to printing graphics onto advancing substrates in absorbent article converting lines, wherein first graphics having relatively low print resolutions and second graphics having relatively high print resolutions may be both printed onto advancing substrates.

In one form, in a method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprises the steps of: advancing a first continuous substrate having a first surface and an opposing second surface in a machine direction at a first speed, and defining a width in a cross direction; inkjet printing a first graphic on the first surface of the first continuous substrate while the first continuous substrate is advancing at the first speed, the first graphic comprising a first print resolution; decelerating a portion of the first continuous substrate to a second speed; inkjet printing a second graphic on the portion of the first surface of the first continuous substrate while at the second speed, the second graphic comprising a second print resolution, wherein the second print resolution is equal to or greater than about 400% of the first print resolution; accelerating the portion of the first continuous substrate from the second speed to the first speed; advancing a second continuous substrate having a first surface and an opposing second surface in the machine direction, and defining a width in the cross direction; bonding elastic strands in a stretched state between the first surface of the first continuous substrate and the first surface of the second continuous substrate to form a continuous elastic laminate; cutting the elastic laminate along the machine direction to form a first continuous elastic laminate and a second continuous elastic laminate, wherein the first continuous elastic laminate includes the first graphic and the second graphic; separating the first continuous elastic laminate in the cross direction from the second continuous elastic laminate; depositing a plurality of chassis spaced apart from each other along the machine direction onto the first continuous elastic laminate and the second continuous elastic laminate; folding each chassis along the lateral axis to position the first continuous elastic laminate into a facing relationship with the second continuous elastic laminate; and cutting the first and second continuous elastic laminates into discrete pieces each having a pitch length, PL, extending along the machine direction, wherein the second graphic extends in the machine direction for 50% or less than the pitch length.

In another form, in a method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprises the steps of: advancing a first continuous substrate having a first surface and an opposing second surface in a machine direction at a first speed, and defining a width in a cross direction; inkjet printing a first graphic on the first continuous substrate while the first continuous substrate is advancing at the first speed, the first graphic comprising a first print resolution; decelerating a portion of the first continuous substrate to a second speed; inkjet printing a second graphic on the portion of the first continuous substrate while at the second speed, the second graphic comprising a second print resolution equal to or greater than about 400% of the first print resolution; accelerating the portion of the first continuous substrate from the second speed to the first speed; advancing a second continuous substrate having a first surface and an opposing second surface in the machine direction, and defining a width in the cross direction; bonding elastic strands in a stretched state between the first surface of the first continuous substrate and the first surface of the second continuous substrate to form a first elastic laminate; depositing a plurality of chassis spaced apart from each other along the machine direction onto the first continuous elastic laminate; folding each chassis along the lateral axis to position the first end region in a facing relationship with the second end region; cutting the first continuous elastic laminate into discrete pieces each having a pitch length, PL, extending along the machine direction, wherein the second graphic extends in the machine direction for 50% or less than the pitch length, PL.

In yet another form, in a method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprises the steps of: advancing a first continuous substrate having a first surface and an opposing second surface in a machine direction at a first speed, and defining a width in a cross direction; inkjet printing a first graphic on the first surface of the first continuous substrate while the first continuous substrate is advancing at the first speed, the first graphic comprising a first print resolution; decelerating a portion of the first continuous substrate to a second speed; inkjet printing a second graphic on the portion of the first surface of the first continuous substrate while at the second speed, the second graphic comprising a second print resolution greater than the first print resolution; accelerating the portion of the first continuous substrate from the second speed to the first speed; advancing a second continuous substrate having a first surface and an opposing second surface in the machine direction, and defining a width in the cross direction; bonding elastic strands in a stretched state between the first surface of the first continuous substrate and the first surface of the second continuous substrate to form a continuous elastic laminate; cutting the elastic laminate along the machine direction to form a first continuous elastic laminate and a second continuous elastic laminate; separating the first continuous elastic laminate in the cross direction from the second continuous elastic laminate; depositing a plurality of chassis spaced apart from each other along the machine direction onto the first continuous elastic laminate and the second continuous elastic laminate; folding each chassis along the lateral axis to position the first continuous elastic laminate into a facing relationship with the second continuous elastic laminate; and cutting the first and second continuous elastic laminates into discrete pieces each having a pitch length, PL, extending along the machine direction, wherein the second graphic extends in the machine direction for 50% or less than the pitch length.

In still another form, an absorbent article comprises: a first elastic belt extending laterally from a first longitudinal end edge to a second longitudinal end edge to define a pitch length, and extending longitudinally from an outer lateral end edge to an inner lateral end edge, the first elastic belt further comprising a first end region and a laterally opposing second end region separated from each other by a central region; a second elastic belt extending laterally from a first longitudinal end edge to a second longitudinal end edge, and extending longitudinally from an outer lateral end edge to an inner lateral end edge, the second elastic belt further comprising a first end region and a laterally opposing second end region separated from each other by a central region; a chassis comprising, a topsheet, a backsheet, and an absorbent core positioned between the topsheet and the backsheet, the chassis further comprising a first waist region and a second waist region separated from each other by a crotch region, wherein the first waist region is connected with the central region of the first elastic belt and the second waist region is connected with the central region of the second elastic belt; a first graphic inkjet printed on the first elastic belt, the first graphic comprising a first print resolution; a second graphic inkjet printed on the first elastic belt, the second graphic comprising a second print resolution, wherein the second print resolution is equal to or greater than about 400% of the first print resolution; and wherein the second graphic extends along the first elastic belt for about 50% or less than the pitch length.

BRIEF DESCRIPTION OF THE DRAWINGS

FIG. 2A is a partially cut away plan view of the diaper pant shown in FIGS. 1A and 1B in a flat, uncontracted state.

FIG. 3A is a cross-sectional view of the diaper pant of FIG. 2A taken along line 3A-3A.

FIG. 3B is a cross-sectional view of the diaper pant of FIG. 2A taken along line 3B-3B.

FIG. 5A1 is a view of a continuous length of an advancing first substrate from FIG. 4 taken along line A1-A1.

FIG. 5A2 is a view of the advancing first substrate with a first graphic from FIG. 4 taken along line A2-A2.

FIG. 5A3 is a view of the advancing first substrate with the first graphic and a second graphic from FIG. 4 taken along line A3-A3.

FIG. 5B is a view of continuous lengths of advancing first and second elastic belt laminates from FIG. 4 taken along line B-B.

FIG. 5C is a view of a continuous length of chassis assemblies from FIGS. 4 and 12 taken along line C-C.

FIG. 5D1 is a view of a discrete chassis from FIGS. 4 and 12 taken along line D1-D1.

FIG. 5D2 is a view of a discrete chassis from FIGS. 4 and 12 taken along line D2-D2.

FIG. 5F is a view of folded multiple discrete chassis with the first and second elastic belt laminates in a facing relationship from FIG. 4 taken along line F-F.

FIG. 5G is a view of two discrete absorbent articles advancing the machine direction MD from FIG. 4 taken along line G-G.

FIG. 10A is a front perspective view of a diaper pant constructed with a contiguous outer cover.

FIG. 10C is a rear plan view of the diaper pant of FIG. 10A.

FIG. 13A1 is a view of a continuous length of an advancing first substrate from FIG. 12 taken along line A1-A1.

FIG. 13A2 is a view of a continuous length of an advancing elastic laminate from FIG. 12 taken along line A2-A2.

FIG. 13E1 is a view of multiple discrete chassis spaced from each other along the machine direction MD and connected with each other by an outer cover and the first and second elastic belt laminates from FIG. 12 taken along line E1-E1.

FIG. 13E2 is a view of multiple discrete chassis spaced from each other along the machine direction MD and connected with each other by an outer cover and the first and second elastic belt laminates from FIG. 12 taken along line E2-E2.

FIG. 13F is a view of folded multiple discrete chassis with the first and second elastic belt laminates in a facing relationship from FIG. 12 taken along line F-F.

FIG. 13G is a view of two discrete absorbent articles advancing the machine direction MD from FIG. 12 taken along line G-G.

DETAILED DESCRIPTION OF THE INVENTION

Figure 1A:
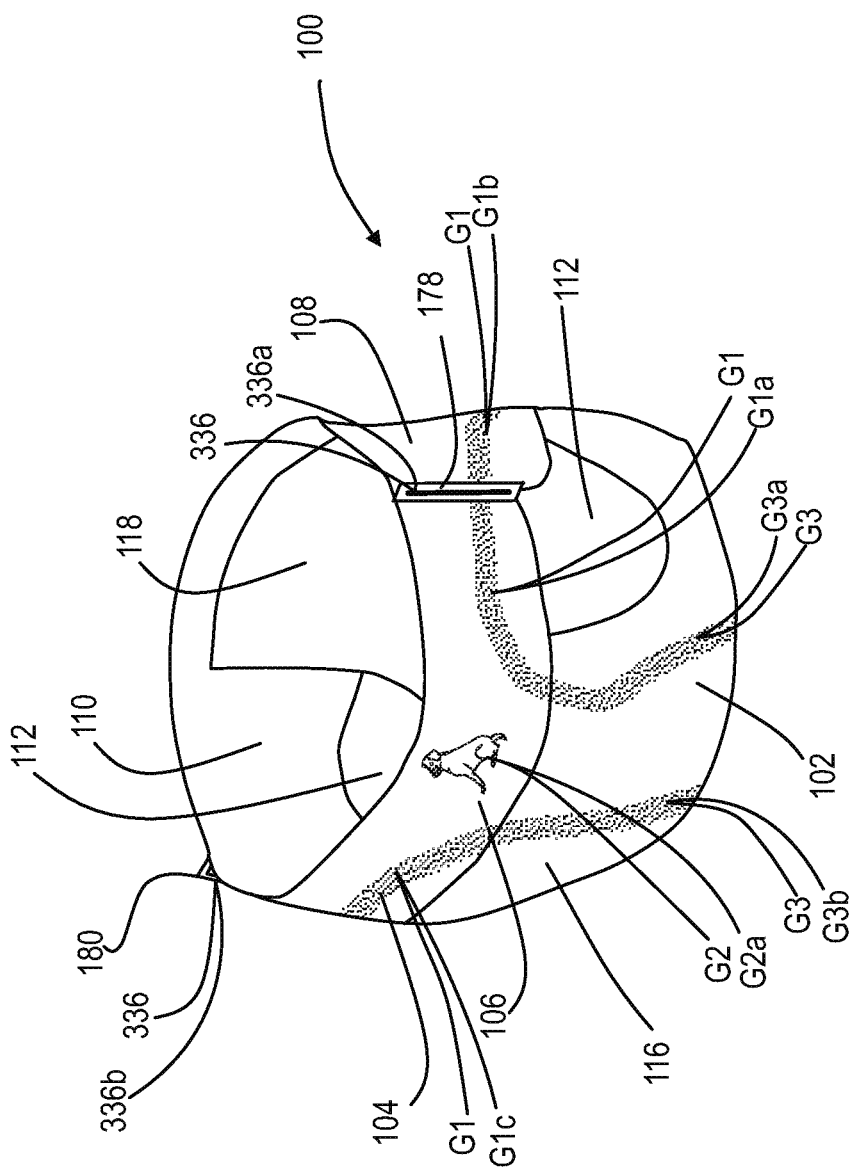
FIG. 1A is a front perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "graphic" refers to images or designs that are constituted by a figure (e.g., a line(s)), a symbol or character, a color difference or transition of at least two colors, or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "print resolution" is defined in terms of inkjet printing technology by Dots Per Inch (DPI), wherein DPI defines a density of dots of ink that can be printed across a one inch length of a substrate to form a printed graphic.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

The present disclosure relates to methods and apparatuses for assembling absorbent articles, and in particular, printing graphics onto advancing substrates in diaper converting lines, wherein the graphics have different print resolutions. More particularly, first graphics having relatively low print resolutions and second graphics having relatively high print resolutions may be both inkjet printed onto advancing substrates, and the printed substrates may be used in the assembly of various diaper components. During the assembly process, localized speed variances may be imparted to the advancing substrates to achieve the different print resolutions, wherein first graphics with relatively low print resolutions may be printed onto the substrate while advancing at relatively high speeds, and second graphics with relatively high print resolutions may be printed onto portions of the substrate that have been temporarily stopped or slowed to relatively slow speed. The printed substrates may then be incorporated into assembled diapers so as place the graphics in desired positions on the diapers. Thus, the second graphics having relatively high print resolutions may be positioned in areas of the diaper that may be more noticeable by consumers, whereas the first graphics having relatively low print resolutions may be positioned in areas of the diaper that may be less noticeable by consumers. For example, second graphics having relatively high print resolutions may be positioned in central portions of front and/or back waist regions, and first graphics having relatively low print resolutions may be positioned in other areas such as crotch regions, waist edges, and/or side seams. As such, the methods and apparatuses herein allow for the use of online inkjet printing techniques in diaper manufacturing processes that maintain desired aesthetic benefits on assembled diapers without sacrificing relatively high manufacturing speeds.

As discussed in more detail below, diapers may each include a chassis connected with front and back elastic belts. The chassis may include a topsheet, a backsheet, and an absorbent core disposed between the topsheet and the backsheet. And printed substrates may be used to assemble continuous elastic laminates, which in turn, form the front and/or back elastic belts. During the elastic belt assembly process, localized speed variances may be imparted to the substrate while printing graphics, resulting in graphics having different print resolutions. In some configurations, a substrate may advance at a first speed past an inkjet printer that prints a first graphic onto the substrate, wherein the first graphic has a first print resolution. The substrate may also advance through an accumulator apparatus that decelerates a portion of the substrate to a second speed that is less than the first speed. While at the second speed, an inkjet printer prints a second graphic onto the portion of the substrate, wherein the second graphic has a second print resolution that is greater than the first resolution. Once the second graphic is printed, the portion of the substrate is then accelerated back to the first speed. The printed substrate is incorporated into an elastic belt assembly process. Opposing end regions of the chassis are then connected with the elastic belts in the form of first and second continuous elastic laminates that may include the printed substrate. The chassis are then folded to place the elastic laminates into a facing relationship. Once the chassis are folded, the first and second continuous elastic laminates are cut in the cross direction to form discrete pant diapers having the printed graphics on the front and/or back elastic belts. In some configurations, chassis components, such as the backsheet, may also include graphics, and during the assembly process, the chassis and elastic laminates may be assembled such that the graphics are aligned to provide the appearance of contiguous designs that extend across more than one component, such as the elastic belts and/or chassis.

As previously mentioned, the processes and apparatuses discussed herein may be used in the manufacture of different types of absorbent articles. To help provide additional context to the subsequent discussion of the process embodiments, the following provides a general description of absorbent articles in the form of diaper pants that include belt substrates that may be assembled in accordance with the methods and apparatuses disclosed herein.

Figure 1B:
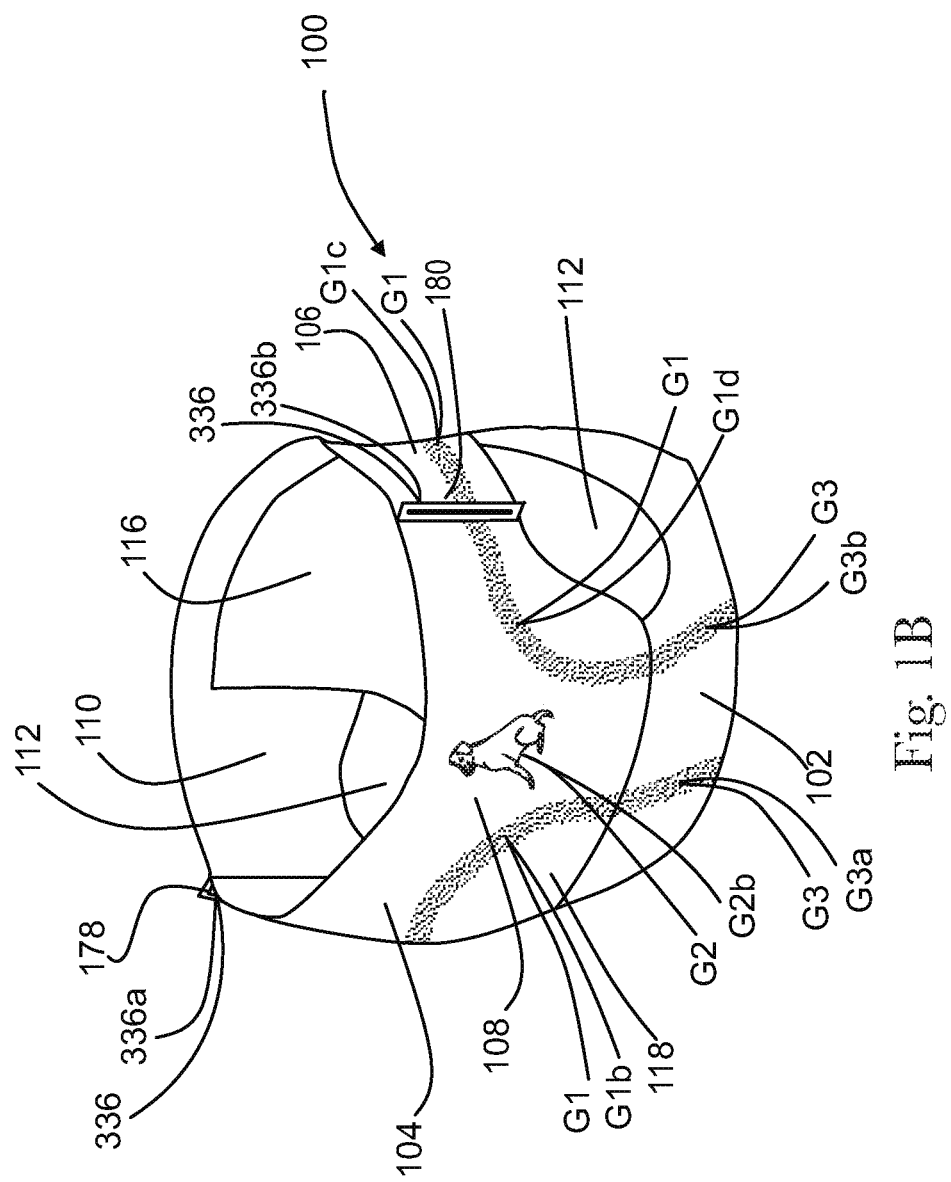
FIG. 1B is a rear perspective view of a diaper pant.
Figure 2B:
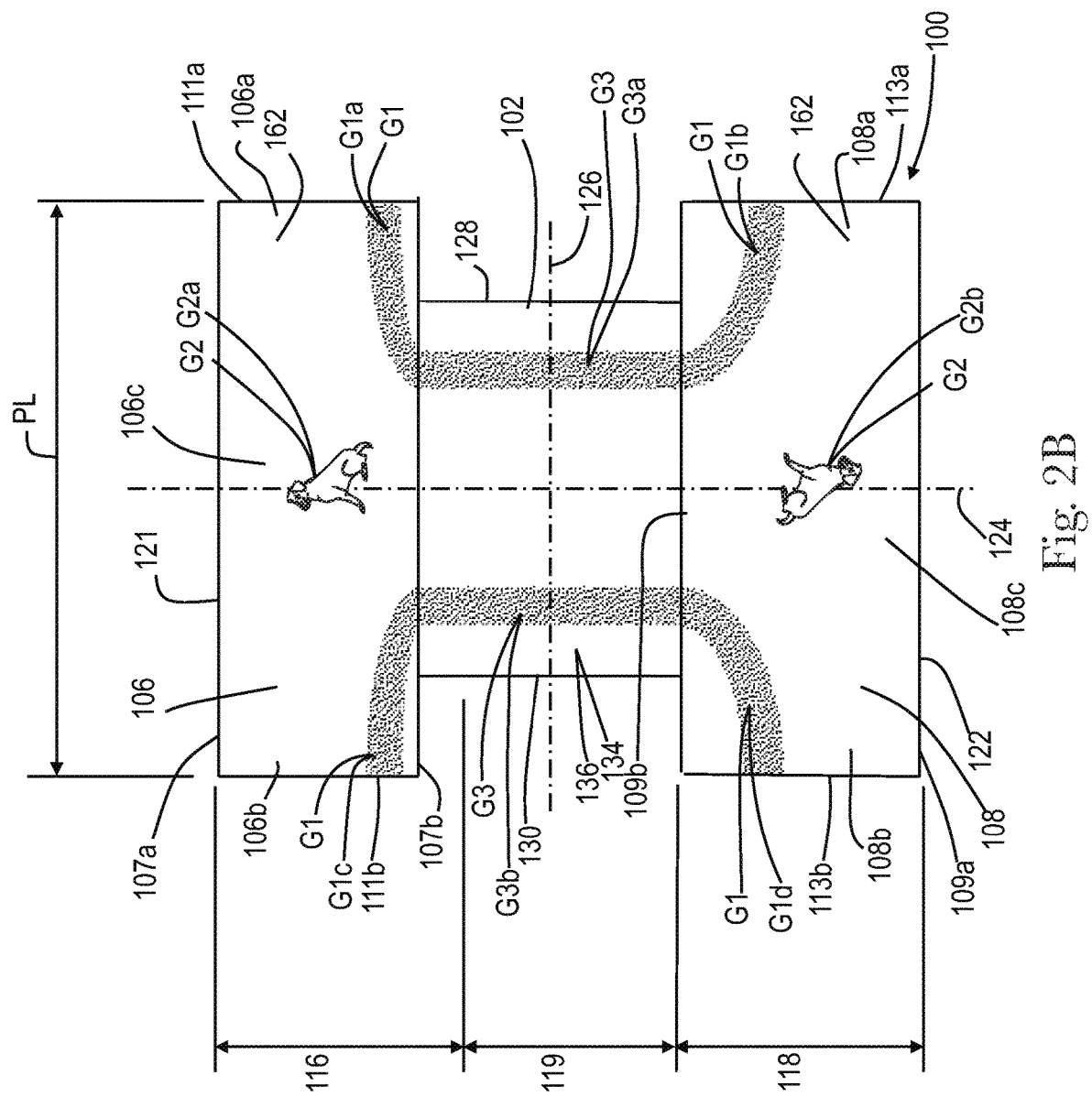
FIG. 2B is a plan view of the diaper pant shown in FIGS. 1A and 1B in a flat, uncontracted state.

FIGS. 1A, 1B, 2A, and 2B show an example of a diaper pant 100 that may be assembled in accordance with the apparatuses and methods disclosed herein. In particular, FIGS. 1A and 1B show perspective views of a diaper pant 100 in a pre-fastened configuration, and FIGS. 2A and 2B show plan views of the diaper pant 100 with the portion of the diaper that faces away from a wearer oriented toward the viewer. The diaper pant 100 includes a chassis 102 and a ring-like elastic belt 104. As discussed below in more detail, a first elastic belt 106 and a second elastic belt 108 are bonded together to form the ring-like elastic belt 104.

With continued reference to FIGS. 2A and 2B, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIGS. 2A and 2B are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, 2A, and 2B, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIGS. 2A and 2B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining the first elastic belt to a second elastic belt with a permanent side seam or with an openable and reclosable fastening system disposed at or adjacent the laterally opposing sides of the belts.

As previously mentioned, the ring-like elastic belt 104 is defined by a first elastic belt 106 connected with a second elastic belt 108. As shown in FIGS. 2A and 2B, the first elastic belt 106 extends between a first longitudinal edge 111a and a second longitudinal edge 111b and defines first and second opposing end regions 106a, 106b and a central region 106c. And the second elastic 108 belt extends between a first longitudinal edge 113a and a second longitudinal edge 113b and defines first and second opposing end regions 108a, 108b and a central region 108c. The distance between the first longitudinal edge 111a and the second longitudinal edge 111b defines the pitch length, PL, of the first elastic belt 106, and the distance between the first longitudinal edge 113a and the second longitudinal edge 113b defines the pitch length, PL, of the second elastic belt 108. The central region 106c of the first elastic belt is connected with the first waist region 116 of the chassis 102, and the central region 108c of the second elastic belt 108 is connected with the second waist region 116 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

It is to be appreciated that the first and second elastic belts may define various pitch lengths PL. For example, in some embodiments, the pitch lengths PL of the first and/or second elastic belts 106, 108 may be about 300 mm to about 1100 mm.

As shown in FIGS. 2A, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. The outer laterally extending edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2A. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107b, 109b.

As previously mentioned, the diaper pant may include one or more graphics. For example, as shown in FIGS. 1A, 1B, and 2B, the diaper pant 100 may include graphics, such as first graphics G1, second graphics G2, and third graphics G3. First graphics G1 are depicted in the form of printed stripes G1a, G1b, G1c, G1d extending along the front and back elastic belts 106, 108. The second graphics G2 are depicted in the form of animals G2a, G2b positioned in the central regions 106c, 108c of the front and back elastic belts 106, 108. And the third graphics G3 are depicted in the form of printed stripes G3a, G3b extending along the chassis 102 and through the crotch region 119 between edges 107b, 109b. As discussed in more detail below, the first graphics G1 and the second graphics G2 may be printed during the diaper assembly process such that the second graphics G2 include a higher print resolution than the first graphics G1. Further, as discussed in more detail below, the diaper 100 may be assembled such that the first elastic belt 106, second elastic belt 108, and chassis 102 are combined so that the stripes G1a, G1b, and G3a appear to be contiguous although each stripe includes multiple portions printed on different diaper components. Similarly, the stripes G1c, G1d, and G3b appear to be contiguous although each stripe includes multiple portions printed on different diaper components. It is to be appreciated that all graphics discussed herein may be in various different forms, shapes, and/or sizes than those depicted herein.

Figure 4:
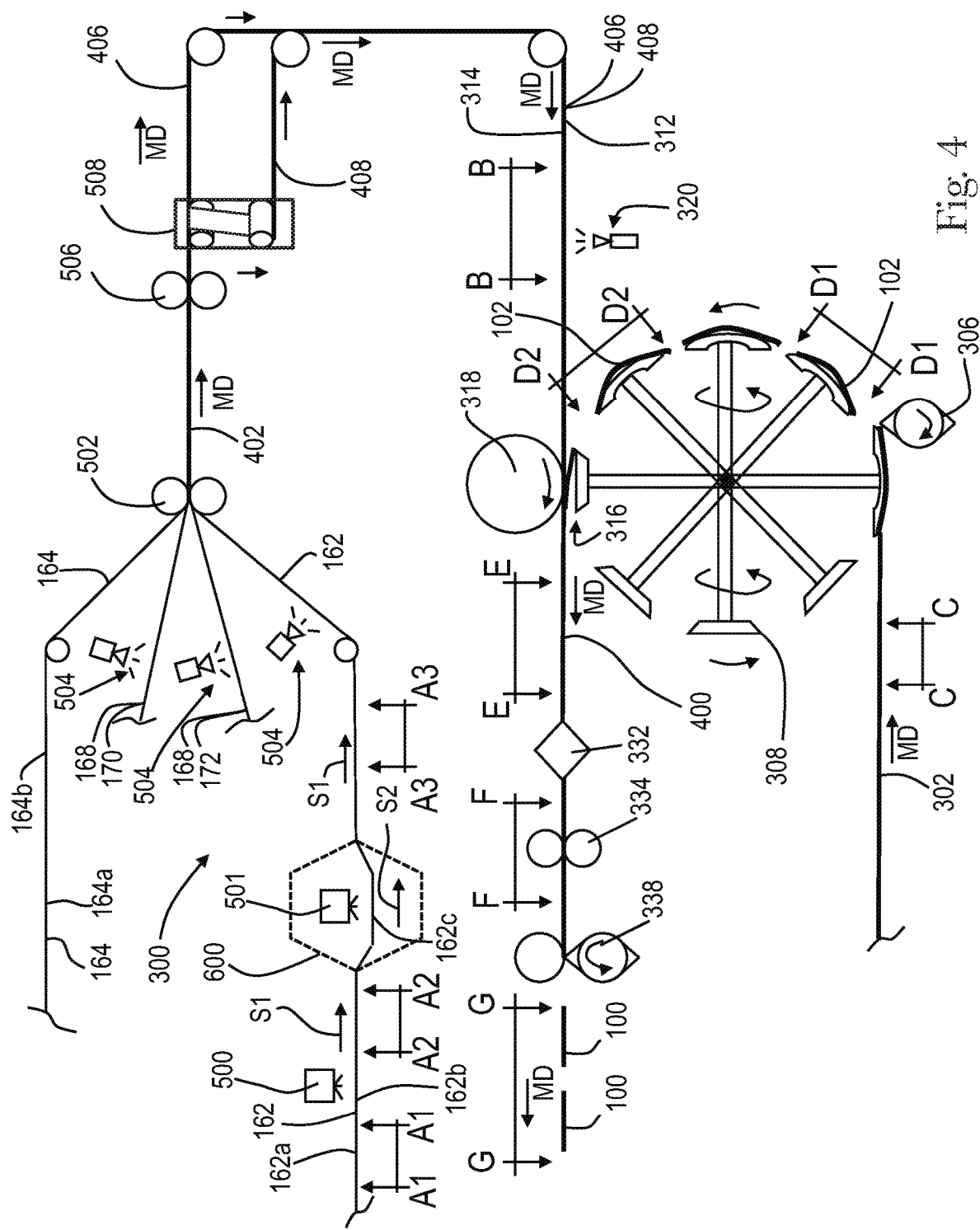
FIG. 4 is a schematic side view of a converting apparatus adapted to manufacture pre-fastened, pant diapers.

As previously mentioned, the apparatuses and methods according to the present disclosure may be utilized to assemble various components of pre-fastened, refastenable pant diapers 100. For example, FIG. 4 shows a schematic view of a converting apparatus 300 adapted to manufacture pant diapers 100. The method of operation of the converting apparatus 300 may be described with reference to the various components of pant diapers 100 described above and shown in FIGS. 1A, 1B, 2A, and 2B. Although the following methods are provided in the context of the diaper 100 shown in FIGS. 1A, 1B, 2A, and 2B, it is to be appreciated that various embodiments of diaper pants can be manufactured according to the methods disclosed herein, such as for example, the absorbent articles disclosed in U.S. Pat. No. 7,569,039; U.S. Patent Publication Nos. 2005/0107764 A1, 2012/0061016 A1, and 2012/0061015 A1, which are all hereby incorporated by reference herein.

As described in more detail below, the converting apparatus 300 shown in FIG. 4 operates to advance first and second elastic belt laminates 406, 408 along a machine direction MD. In addition, a continuous length of chassis assemblies 302 are advanced in a machine direction MD and cut into discrete chassis 102 such that the longitudinal axis of each chassis 102 is parallel with the machine direction MD. The discrete chassis 102 are then turned to advance the discrete chassis 102 along the machine direction MD such that the lateral axis of each chassis 102 is parallel with the machine direction MD. The discrete chassis 102 are also spaced apart from each other along the machine direction MD. Opposing waist regions 116, 118 of the spaced apart chassis 102 are then connected with continuous lengths of advancing first and second elastic belt laminates 406, 408. The chassis 102 may then be folded along the lateral axis, or parallel to the lateral axis, to bring the first and second elastic belt laminates 406, 408 into a facing relationship, and the first and second elastic belt laminates are bonded together with laterally opposing bonds 336. As discussed in more detail below, the first and second elastic belt laminates may be bonded together with adjacent bonds 336a, 336b intermittently spaced along the machine direction MD. Each bond 336a, 336b may be a discrete bond site extending contiguously in a cross direction CD across a width of the first and second elastic belt laminates and/or may include a plurality of relatively small, discrete bond sites arranged in the cross direction. The first and second continuous elastic laminates 406, 408 are then cut in the cross direction CD between adjacent bonds 336a, 336b to create discrete pant diapers 100, such as shown in FIGS. 1A and 1B.

As shown in FIG. 4, a first continuous substrate layer in the form of a continuous length of outer layer belt material 162; a second continuous substrate layer in the form of a continuous length of inner layer belt material 164; and elastics 168 are combined to form a continuous elastic laminate in the form of a belt material 402. More particularly, continuous lengths of outer layer belt material 162, inner layer belt material 164, outer elastic strands 170 and inner elastic strands 172 are advanced in a machine direction MD and combined at nip rolls 502 to form a continuous length of belt material 402.

Before entering the nip rolls 502, the outer layer belt material 162 and/or the inner belt material 164 may be printed with graphics having different print resolutions. For example, as shown in FIG. 4, the outer belt material 162 includes first surface 162a and an opposing second surface 162b. And the outer belt material 162 may advance in the machine direction at a first speed S1 past a first printing station 500 that prints a first graphic G1 on the first surface 162a of the outer belt material 162. The first graphic G1 includes a first print resolution. From the printing station 500, the outer layer belt material 162 advances through an accumulator apparatus 600 that decelerates a portion 162c of the outer layer belt material 162 to a second speed S2 less than first speed $S_1$. While at the second speed S2, a second printing station 501 prints a second graphic G2 on the first surface 162a of the portion 162c of the outer layer belt material 162, such as shown in FIG. 4. The second graphic G2 has a second print resolution. As shown in FIG. 5A3, the second graphic may also extend a maximum length GL in the machine direction MD. Once the second graphic G2 is printed, the outer layer belt material 162 is accelerated back to the first speed S1 and exits the accumulator apparatus 600. As shown in FIGS. 4 and 5A1-5A3, although the first graphics G1 and second graphics G2 are printed on the first surface 162a of the outer layer belt material 162, the first graphics G1 and second graphics G2 may be visible through the second surface 162b. Because the first graphics G1 are printed while the outer layer belt material 162 is advancing at relatively high speed S1 and the second graphics G2 are printed while the outer layer belt material 162 is advancing at a relatively low speed S2, the second print resolution is greater than the first print resolution.

It is to be appreciated that the printing stations 500, 501 herein may be configured in various ways and may include various types of printing accessories. For example, in some embodiments, the printing stations 500, 501 may include a printer in the form of an ink-jet printer. Ink-jet printing is a non-impact dot-matrix printing technology in which droplets of ink are jetted from a small aperture directly to a specified position on a media to create a graphic. Two examples of inkjet technologies include thermal bubble or bubble jet and piezoelectric. Thermal bubble uses heat to apply to the ink, while piezoelectric uses a crystal and an electric charge to apply the ink. In some configurations, the printing stations 500, 501 may include a corona treater, which may be positioned upstream of the printer. The corona treater may be configured to increase the surface energy of the surface of the substrate to be printed. In some embodiments, the corona treater may be configured to increase the surface energy of the surface to be printed to about 42 dynes/cm. In some configurations, the printing stations 500, 501 may also include an ink curing apparatus. In some configurations, the ink curing apparatus may be in the form of an ultraviolet (UV) light source that may include one or more ultraviolet (UV) lamps, which may be positioned downstream of the printer to help cure inks deposited onto the substrate from the printer to form the graphics. In some configurations, the ink curing apparatus may also include an infrared (IR) dryer light source that may include one or more infrared (IR) lamps, which may be positioned downstream of the printer to help dry water-based or solvent-based inks deposited onto the substrate to form the graphics. In some configurations, the ink curing apparatus may include an electron beam (EB or e-beam) generator that may include one or more e-beam electrodes, which may be positioned downstream of the printer to help cure inks deposited onto the substrate from the printer to form the graphics.

In some configurations, either or both the printing stations 500, 501 may be adapted to interface with a computer that allows an operator to manually program the type of graphics to be printed. For example, the printing station may be configured with various features, such as available on the XD070 Multi-Color Industrial Ink Jet unit available from Pad Print Machinery of Vermont. In some configurations, the printing station may be configured to interface with other computerized systems and/or networks that may automatically program or command the printing station to print various graphics based on various input, such as sales orders from customers.

It is to be appreciated that the first printing station 500 may be positioned downstream of the second printing station 501 such that first graphics G1 are printed subsequent to the second graphics G2. It is also to be appreciated that the first graphics G1 and/or second graphics G2 may be printed on either or both the first and second surfaces 162a, 162b of the outer belt material 162. It is also to be appreciated that the first and/or second printing stations 500, 501, and/or additional printing stations, may be arranged to print graphics on either or both the first and second surfaces 164a, 164b of the inner belt material 164.

It is also to be appreciated that more than one substrate may be printed, and as such, the substrates may have different properties, such as basis weights, fiber characteristics, and/or surface coatings. In addition, different types of printing may be applied to the substrates. For example, one substrate may be printed with flexography and/or gravure printing processes, while another substrate may be printed with inkjet printing processes. It is to be appreciated that the printing may be done during the assembly process and/or may done separate to the assembly process, such as for example, printing the substrates off line wherein the printed substrates may be stored until needed for production. In some instances, customized graphic printing processes may also be utilized, for example such as disclosed in U.S. Pat. No. 8,776,683.

Figure 6:
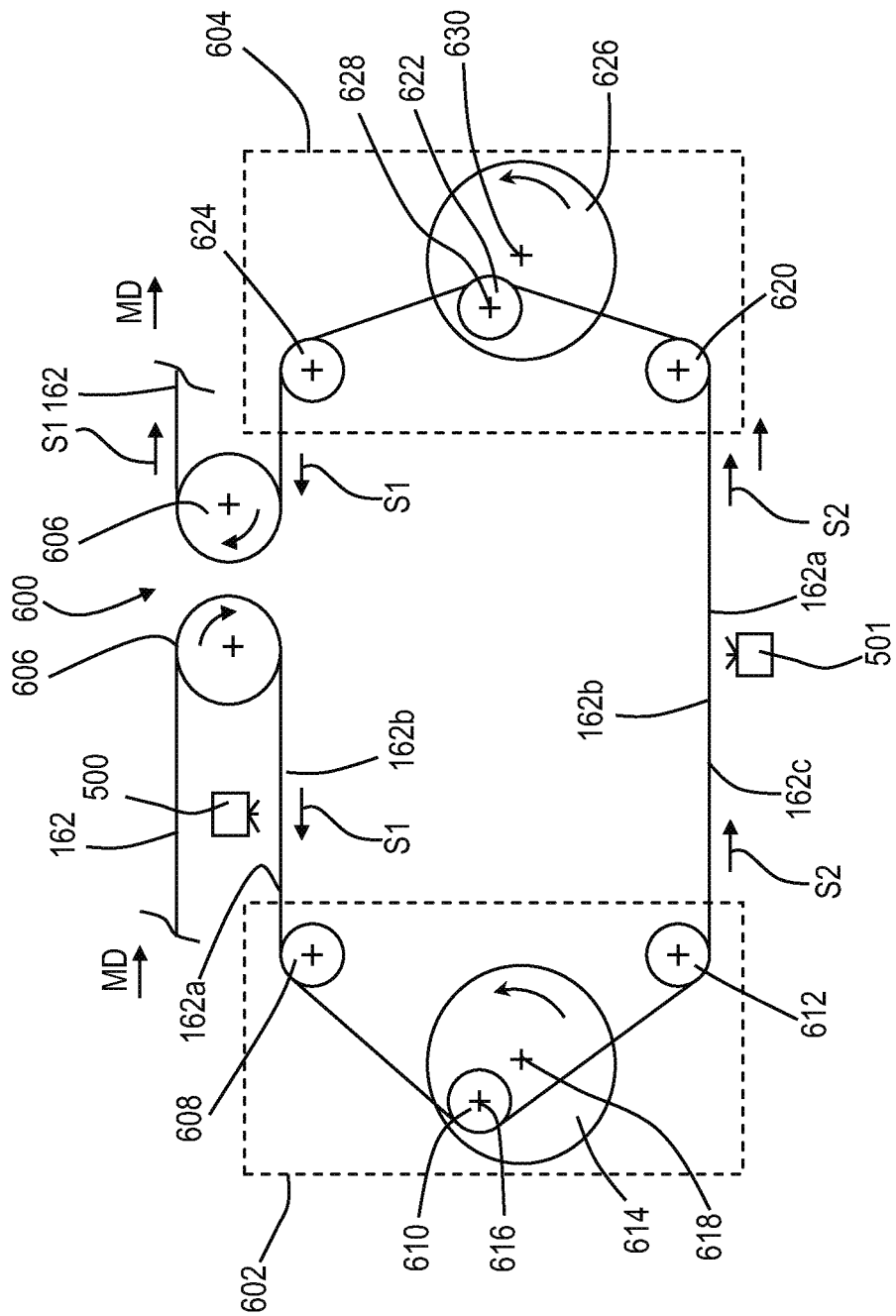
FIG. 6 is a detailed view of an accumulator apparatus.

As previously mentioned, the processing line 300 may include an accumulator apparatus 600, wherein the substrate 162 advances at a first speed S1 past the first printing station 500, and decelerating a portion 162c of the substrate 162 to a second speed S2 while advancing past the second printing station 501. It is to be appreciated that the accumulator apparatus 600 may be configured in various ways for example such as disclosed in U.S. Pat. Nos. 5,373,761; 5,693,165; 6,596,108; 6,620,276; 6,349,867; and 8,377,249. For example, FIG. 6 shows an example accumulator apparatus 600 for varying the speed of the advancing substrate 162. As such, the apparatus 600 may be configured to provide localized speed changes of the substrate 162. For example, the apparatus 600 may provide localized speed changes of the substrate 162 as the substrate 162 advances past the second printing station 501. As shown in FIG. 6, the apparatus 600 may include a first substrate guide 602 and a second substrate guide 604. The substrate 162 advances in the machine direction (MD) around an idler roller 606, past the first printing station 500, and enters the first substrate guide 110 at a first speed $S_1$. The substrate 162 travels from the first substrate guide 602 at a second speed $S_2$ past the second printing station 501. From the second printing station 501, the substrate 162 enters the second substrate guide 604. The substrate 162 then exits the second substrate guide 604 at the first speed $S_1$. As discussed in more detail below, the first substrate guide 602 and second substrate guide 604 operate to change the lengths of the substrate within the respective guides, and thus, vary the second speed $S_2$ of the substrate traveling from the upstream, first substrate guide 602 to the downstream, second substrate guide 604. At the same time, the speed of the substrate entering the first substrate guide and exiting the second substrate guide is maintained at a constant first speed $S_1$. The idler rollers 606 in FIG. 6 show only one example of how the substrate 162 may be advanced to and from the apparatus 600, and as such, it is to be appreciated that various other configurations and arrangements can be utilized.

As previously mentioned, the second speed $S_2$ of the substrate 162 can be varied as the substrate travels past the second printing station 501. As discussed in more detail below, the first and second substrate guides 602, 604 may be configured to periodically slow (e.g. second speed, S2, is slower than the first speed, $S_1$) the movement of the portion 162c of the substrate 162 in the machine direction (MD) advancing past the second printing station 501. In some configurations, the first and second substrate guides 602, 604 may be configured to periodically stop (e.g. second speed, S2, is zero) the movement of the portion 162c of the substrate 162 in the machine direction (MD) advancing past the second printing station 501.

As described in more detail below, the substrate guides 602, 604 may be configured to touch only one side of the substrate 162. For example, the first and second substrate guides 602, 604 may be configured to touch only the second surface 162b of the substrate 162, and do not touch the first surface 162a of the substrate 162. Such a configuration may be beneficial to reduce negative impacts on the printing operations performed on the substrate 162. For example, FIG. 6 shows the first printing station 500 printing first graphics G1 on the first surface 162a of the substrate 162 before the substrate enters the first substrate guide 602. And the second printing station 500 is depicted as printing second graphics G2 on the first surface 162a of the substrate 162 before the substrate enters the second substrate guide 604. Because the first and second substrate guides 602, 604 touch only the second surface 162b of the substrate 162, risks of contaminating or otherwise affecting the printed graphics G1, G2 on the first surface 162a may be reduced.

As shown in FIG. 6, the first substrate guide 602 includes a first guide member 608 in the form of a first roller, a second guide member 610 in the form of a second roller, and a third guide member 612 in the form of a third roller 130. As described below, the substrate 102 travels in the machine direction (MD) at the first speed $S_1$ to the first roller 608; from the first roller 608 to the second roller 610; from the second roller 610 to the third roller 612; and from the third roller 612 to the second printing station 501 and to the second substrate guide 604 at the second speed S2. As shown in FIG. 6, the second roller 610 is rotatably connected with a support member 614 at a second roller axis 616. The support member 614 is adapted to rotate around a second center axis 618. As such, the second roller 610 orbits around the second center axis 618 as the support member 614 rotates. As the substrate 162 advances through the first substrate guide 602, only the second surface 162b of the substrate 162 contacts the outer radial surfaces of the first, second, and third rollers 608, 610, 612.

Similar to the first substrate guide 602, the second substrate guide 604 includes a first guide member 620 in the form of a first roller, a second guide member 622 in the form of a second roller, and a third guide member 624 in the form of a third roller. As described below, the substrate 162 travels in the machine direction at the second speed $S_2$ (from the first substrate guide 602 and past the second printing station 501 to the first roller 620; from the first roller 620 to the second roller 622; from the second roller 622 to the third roller 624; and from the third roller 624 to continue downstream at the first speed $S_1$. As shown in FIG. 6, the second roller 622 is rotatably connected with a support member 626 at a second roller axis 628. The support member 626 is adapted to rotate around a second center axis 630. As such, the second roller 622 orbits around the second center axis 630 as the support member 626 rotates. As the substrate 162 advances through the second substrate guide 604, only the second surface 162b of the substrate 162 contacts the outer radial surfaces of the first, second, and third rollers 620, 622, 624.

Although the guide members 608, 610, 612, 620, 622, 624 of the first and second substrate guides 602, 604 are shown and described as rollers, it is to be appreciated that the guide members can be configured in other ways. For example, in some embodiments, the guide members may be configured as rollers, stationary pins or rods, endless belts, spheres, and/or combinations thereof. In addition, although the support members 614, 626 are shown in the form of wheels, it is to be appreciated that the support members may be configured in other ways, such as for example, an elongate member or rotating arm. Further, some or all of the rollers can be driven rollers, idler rollers, and/or combinations of each. In addition, the support members can be rotated at constant or variable speeds. In some embodiments, the support members 614, 626 may have separate and/or variable speed drives, such as for example, servo motors.

As mentioned above, the first substrate guide 602 and the second substrate guide 604 utilize orbital motion of guide members to change the length of the substrate 162 within the substrate guides. In particular, rotation of the support members 614, 626 causes the second rollers 610, 622 to orbit around the second center axes 618, 630. In turn, the orbital motions of the second rollers 610, 622 result in changes of the lengths of substrate within the substrate guides 602, 604. As such, the coordinated rotation of the support members 614, 626 of the first and second substrate guides 602, 604 result in localized speed changes of the substrate 162 advancing past the second printing station 501 (i.e. a variable second speed, S2), while maintaining a constant first speed, $S_1$.

Figure 7:
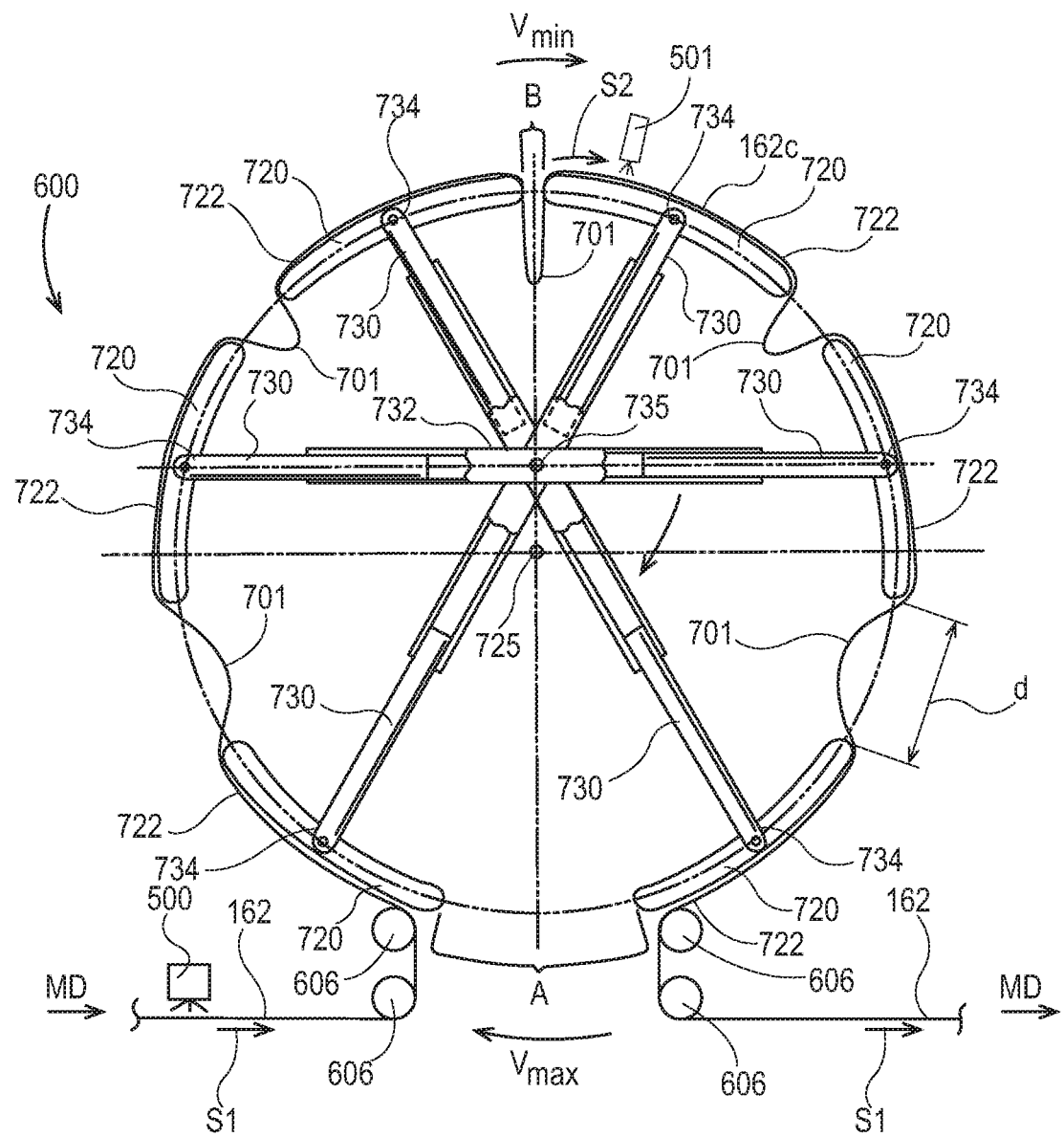
FIG. 7 is a detailed view a second embodiment of an accumulator apparatus.

FIG. 7 shows another example of an accumulator apparatus 600 for varying the speed of the advancing substrate 162 similar to the apparatus disclosed in U.S. Pat. No. 6,620,276. As such, the apparatus 600 may be configured to provide localized speed changes of the substrate 162 as the substrate 162 advances past the second printing station 501. As shown in FIG. 7, the accumulator apparatus 600 includes web support plates 720 connected with extendible arms 730, wherein each web support plate 720 comprises a web support surface 722 facing outwardly. As discussed in more detail below, the extendible arms 730 rotate the support plates 720 such that the web support surfaces 722 trace out an essentially circular path around a principal axis 725. Each extendible arm 730 has a proximal end 732 and a distal end 734, the proximal end 732 of each extendible arm 730 rotatably connected with a second axis of rotation 35 and the distal end 734 of each extendible arm 730 being pivotally connected with a web support plate 720.

As shown in FIG. 7, the principal axis 725 and the second axis 735 are parallel and off-set in relation to each other, and as such, the extendible arms 730 drive the web support plates 720 around the circular path with a variable circumferential velocity. As a web support plate 720 passes through point A of the circular path (at the bottom of the circular path as illustrated in FIG. 7), the web support plate 720 has a maximum circumferential velocity Vmax. As the web support plate 720 is rotated towards the top of the circular path, the web support plate 720 is decelerated until reaching a minimum circumferential velocity Vmin at point B of the circular path. As the web support plate 720 continues around the circular path, the web support plate 720 is accelerated again to Vmax while returning to point A. Also, as shown in FIG. 7, adjacent web support plates 720 are spaced apart by a distance d. The adjacent web support plates either side of point A in FIG. 7 have a maximum distance d between each other. As the web support plates 720 are rotated, one of the web support plates 720 has a faster circumferential velocity than an adjacent web support plate, and the faster web support plate catches up with the slower web support plate, thereby reducing the distance d between the adjacent web support plates 720. The adjacent web support plates either side of point B in FIG. 7 have a minimum distance d between each other.

With continued reference to FIG. 7, the substrate 162 advances in the machine direction (MID) a first speed $S_1$ past the first printing station 500, around two idler rollers 606, and onto the web support surfaces 722 of the rotating web support plates 720. As the substrate 162 is advanced around the circular path by the decelerating web support plates 720, loops are formed between adjacent web support plates 720. As the web support plates rotate, a portion 162c of the substrate 162 advances past the second printing station 501 at the second speed S2, wherein $S_2$ is less than $S_1$. Subsequently, the web support plates 720 and substrate 162 accelerate, thereby removing the loops between adjacent web support plates 720. The substrate 162 then advances from the support plates 720 at the first speed $S_1$ around two idler rollers 606, and onto the remainder of the assembly process.

As previously mentioned, the first graphics G1 may be printed on the substrate 162 while advancing at a first speed S1, and the second graphics G2 may be printed on a portion 162c of the substrate 162 while advancing at a second speed S2, wherein the second speed S2 is less than the first speed S1. It is to be appreciated that system may be configured with various relative differences between the first speed and second speeds. For example, in some configurations, the second speed S2 is from about 25% to about 50% of the first speed S1. In some configurations, the second speed S2 is about 25% of the first speed S1. Also as mentioned above, the second print resolution of the second graphics G2 is greater than the first print resolution of the first graphics G1, because the first graphics G1 are printed while the substrate 162 is advancing at relatively high speed S1 and the second graphics G2 are printed while the portion 162c of the substrate 162 is advancing at a relatively low speed S2. Thus, it is to be appreciated that system may be configured with various relative differences between the first and second print resolutions. For example, in some configurations, the second graphic G2 may have a second print resolution that is equal to or greater than about 400% of the first print resolution of the first graphic G1. In some configurations, the second graphic G2 may have a second print resolution that is equal to or greater than about 200% of the first print resolution of the first graphic G1. In some configurations, the second graphic G2 may have a second print resolution that is from about 200% to about 500% of the first print resolution of the first graphic G1. In some configurations, the first print resolution is from about 20% to about 50% of the second print resolution. In some configurations, the first print resolution is from about 25% to about 75% of the second print resolution. In some configurations, the first print resolution may be from about 80 dots per inch (DPI) to about 200 dots per inch (DPI); and the second print resolution may be equal to or greater than about 400 dots per inch (DPI). In one example, a print station capable of printing at a 400 dots per inch (DPI) resolution on a substrate advancing at 1.5 m/s may print at a 200 dots per inch (DPI) resolution on a substrate advancing at 3 m/s, and may print at a 100 dots per inch (DPI) resolution on a substrate advancing at 6 m/s.

Referring back to FIG. 4, before entering the nip rolls 502, the outer elastic strands 170 and inner elastic strands 172 are stretched in the machine direction MD. In addition, adhesive 504 may be applied to the elastic strands 170, 172 as well as either or both of the continuous lengths of outer layer belt material 162 and inner layer belt material 164 before entering nip rolls 502. As such, the elastic strands 168 are bonded between the first surface 162a of the outer layer belt material 162 and the first surface 164a of inner layer belt material 164 at the nip rolls 502. Further, adhesive 504 may be applied intermittently along the lengths of the inner elastic strands 172 and/or intermittently along the length of either or both of the continuous lengths of outer layer belt material 162 and inner layer belt material 164 before entering nip rolls 502. As such, the inner elastic strands 172 may be intermittently bonded to either or both of the continuous lengths of outer layer belt material 162 and inner layer belt material 164 along the machine direction MD. Thus, the belt material 402 may include non-bonded regions intermittently spaced between bonded regions along the machine direction MD, wherein the inner elastic strands 172 are not bonded to either the outer layer belt material 162 or inner layer belt material 164 in the non-bonded regions. And the inner elastic strands 172 are bonded to the outer layer belt material 162 and/or inner layer belt material 164 in the bonded regions. Although FIG. 4 shows an embodiment wherein the belt material 402 is formed by combining continuous lengths of outer layer belt material 162 and inner layer belt material 164 with elastic strands 168, it is to be appreciated the belt material 402 can be formed in various ways, such as disclosed in U.S. Pat. No. 8,440,043 and U.S. Patent Publication Nos. 2013/0255861 A1; 2013/0255862 A1; 2013/0255863 A1; 2013/0255864 A1; and 2013/0255865 A1.

With continued reference to FIG. 4, from the nip rolls 502 the continuous length of belt material 402 advances in the machine direction MD to a cutter 506 that cuts the belt material 402 into two continuous belt substrates, referred to as a first belt substrate 406 and a second belt substrate 408. The cutter 506 may be configured in various ways. For example, in some embodiments the cutter 506 may be a slitter or a die cutter that separates the belt material into two continuous belt substrates with either a straight line cut and/or a curved line cut. The cutter 506 may also be configured as a perforator that perforates the belt material with a line of weakness and wherein the belt material is separated along the line of weakness in a later step. From the cutter 506, the first and second belt substrates 406, 408 advance through a diverter 508 that separates the first and second belt substrates from each other in the cross direction CD, such as shown in FIG. 5B. The elastic strands 170, 172, and thus, the continuous length of first and second belt substrates 406, 408 are maintained in a stretched condition while advancing along the machine direction MD. It is to be appreciated that the diverter 508 may be configured in various ways. For example, in some embodiments, the diverter 508 may include turn bars angled at 45 degrees or some other angle with respect to the machine direction. In some embodiments, the diverter may include cambered rollers. It is to be appreciated that the front and back belts may be formed by separate continuous lengths of belt material similar to the description above and as such would not required the slitting step or the diverting step.

In some embodiments, the diverter 508 may include a pivot or tracking table, such as for example, the FIFE-500 Web Guiding System, by Maxcess-FIFE Corporation, which can adjust the positions of the continuous length of first and second belt substrates 406, 408 in the cross direction CD. Other suitable pivot or tracking tables are available from Erhardt & Leimer, Inc. The diverter may also include instrumentation and web edge control features that allow for precise active control of the substrate positions.

As shown in FIG. 5B, the first belt substrate 406 includes an outer longitudinal edge 107a and an inner longitudinal edge 107b that may define a substantially constant width, W1, in the cross direction CD. And the second belt substrate 408 includes an outer longitudinal edge 109a and an inner longitudinal edge 109b that may define a substantially constant width, W2, in the cross direction CD, wherein W2 is greater than W1. It is to be appreciated that in some configurations, W1 may be equal to or greater than W2. As previously mentioned, the first belt substrate 406 is separated in the cross direction from the second belt substrate 408 to define a gap between the inner longitudinal edge 107b of the first belt substrate 406 and the inner longitudinal edge 109b of the second belt substrate 408. As discussed in more detail below, the first and second belt substrates 406, 408 advance from the diverter 508 to a nip 316 between the carrier apparatus 308 and a roll 318 to be combined with discrete chassis 102.

In some configurations, the first and second graphics G1, G2 may be positioned on the continuous length of belt material 402 such that cutter 506 may cut through neither, one, or both of the first and second graphics G1, G2. For example, as shown in FIGS. 4 and 5B, the cutter may 506 may slit the continuous length of belt material 402 along the machine direction MD through the first graphics G1, such that a first portion of the of the first graphic G1 remains with the first belt substrate 406, and a second portion of the first graphic G1 remains with the second belt substrate 408. As depicted in FIG. 5B, the second graphics G2 are not slit by the cutter such that an entire second graphic G2 remains with the first belt substrate 406, and an entire second graphic G2 remains with the second belt substrate 408. It is to be appreciated however that in some configurations, the cutter may 506 may slit the continuous length of belt material 402 along the machine direction MD through the second graphics G2, such that a first portion of the of the second graphic G2 remains with the first belt substrate 406, and a second portion of the second graphic G2 remains with the second belt substrate 408. It should also be appreciated that the cutter may slit the continuous length of belt material 402 without cutting either the first or second graphics G1, G2.

As shown in FIGS. 4 and 5C, a continuous length of chassis assemblies 302 are advanced in a machine direction MD and define a width in a cross direction CD. The continuous length of chassis assemblies 302 may include absorbent assemblies 140 sandwiched between topsheet material 138 and backsheet material 136, leg elastics, barrier leg cuffs and the like. As shown in FIG. 5C, portion of the chassis assembly is cut-away to show a portion of the topsheet material 138 and an absorbent assembly 140. The continuous length of chassis assemblies 302 advance to a carrier apparatus 308 and are cut into discrete chassis 102 with knife roll 306, while advancing in the orientation shown in FIG. 5D1, wherein the longitudinal axis 124 of each chassis 102 is generally parallel with the machine direction MD.

In some embodiments, the converting apparatus 300 may include a pivot or tracking table 301, such as for example, the FIFE-500 Web Guiding System, by Maxcess-FIFE Corporation, which can adjust the positions of the continuous length of chassis assemblies 302 in the cross direction CD. Other suitable pivot or tracking tables are available from Erhardt & Leimer, Inc.

After the discrete absorbent chassis 102 are cut by the knife roll 306, the carrier apparatus 308 rotates and advances the discrete chassis 102 in the machine direction MD in the orientation shown in FIG. 5D1. While the chassis 102 shown in FIG. 5D1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. In changing the chassis orientation, the carrier apparatus 308 may turn each chassis 102 such that the lateral axis 126 of the chassis 102 is parallel or generally parallel with the machine direction MD, such as shown in FIG. 5D2. The carrier apparatus 308 may also change the speed at which the chassis 102 advances in the machine direction MD to a different speed. FIG. 5D2 shows the orientation of the chassis 102 on the carrier apparatus 308 while advancing in the machine direction MD. More particularly, FIG. 5D2 shows the chassis 102 with the lateral axis 126 of the chassis 102 generally parallel with the machine direction MD, and wherein the second longitudinal side edge 130 is the leading edge and the first longitudinal side edge 128 is the trailing edge. It is to be appreciated that various forms of carrier apparatuses may be used with the methods herein, such as for example, the carrier apparatuses disclosed in U.S. Pat. No. 7,587,966 and U.S. Patent Publication Nos. 2013/0270065 A1; 2013/0270069 A1; 2013/0270066 A1; and 2013/0270067 A1. As discussed below, in some embodiments, the carrier apparatus 308 may rotate at a variable angular velocity that may be changed or adjusted by a controller in order to change the relative placement of the chassis 102 and the advancing belt laminates 406, 408.

As previously mentioned, the chassis 102 may also include third graphics G3. For example, as shown in FIG. 5C, the continuous length of chassis assemblies 302 may include third graphics G3 printed thereon. It is to be appreciated that the third graphics may be printed on various chassis components, such as the backsheet 136, and may be printed prior to or during assembly of the chassis components. In some configurations, the third graphics G3 may be printed on a backsheet film layer that is subsequently covered by a nonwoven layer such that the third graphics are visible through the nonwoven layer. It is also to be appreciated that the various printed processes may be used to print the third graphics G3, such as for example, ink jet, flexography, and/or gravure printing processes. As shown in FIGS. 5C, 5D1, and 5D2, the third graphics G3 may be configured as discrete stripes that do not extend the entire length of the individual chassis 102. In some embodiments, the third graphics G3 may be printed to continuously extend the entire lengths of the chassis 102.

As discussed below with reference to FIGS. 4, 5E, 5F, and 5G, the chassis 102 are transferred from the carrier apparatus 318 and combined with advancing, continuous lengths of belt laminates 406, 408, which are subsequently cut to form first and second elastic belts 106, 108 on diapers 100.

Figure 5E:
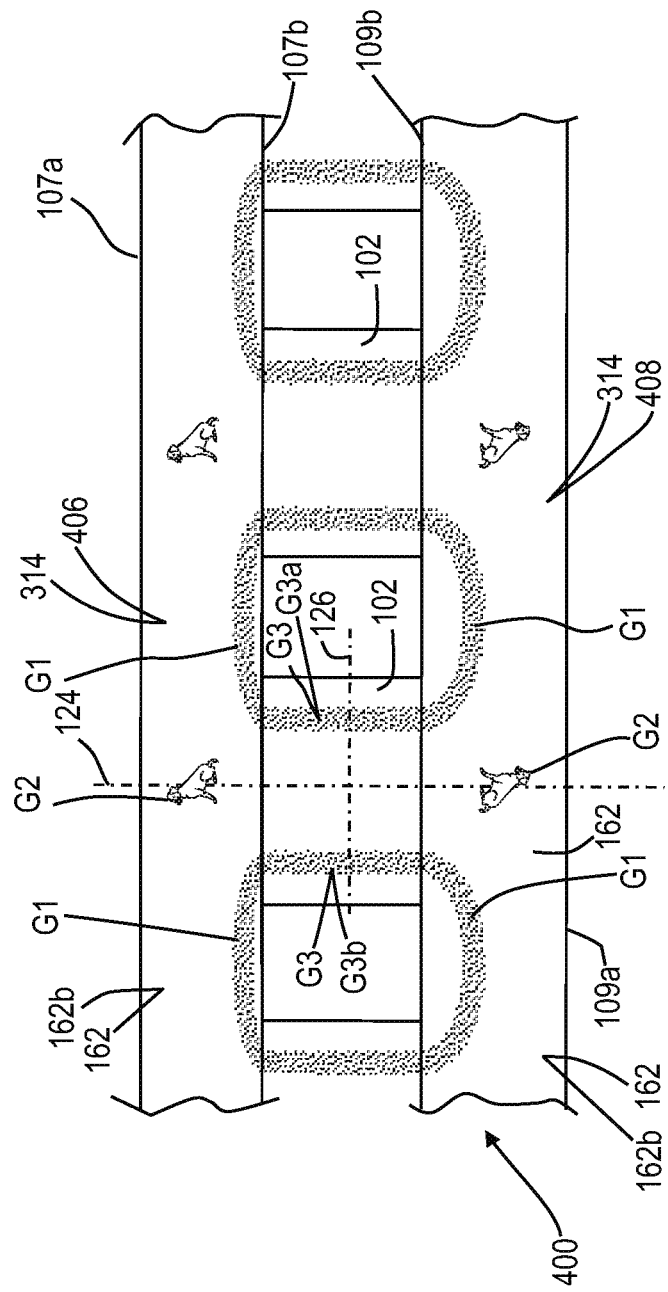
FIG. 5E is a view of multiple discrete chassis spaced from each other along the machine direction MD and connected with each other by the first and second elastic belt laminates from FIG. 4 taken along line E-E.

With reference to FIGS. 4, 5B, and 5E, the chassis 102 are transferred from the carrier apparatus 308 to a nip 316 between the carrier apparatus 308 and a roll 318 where the chassis 102 is combined with continuous lengths of advancing front belt 406 and back belt 408 substrate material. The front belt laminate material 406 and the back belt laminate material 408 each include a wearer facing surface 312 and an opposing garment facing surface 314. As such, the second surface 162b of the outer layer belt material 162 may define the garment facing surface 314, and the second surface 164b of the inner layer belt material 164 may define the wearer facing surface 312. The wearer facing surface 312 of the first belt laminate 406 may be combined with the garment facing surface 134 of the chassis 102 along the first waist region 116, and the wearer facing surface 312 of the second belt laminate 408 may be combined with the garment facing surface 134 of the chassis 102 along the second waist region 118. As shown in FIG. 4, adhesive 320 may be intermittently applied to the wearer facing surface 312 of the first and second belt laminates 406, 408 before combining with the discrete chassis 102 at the nip 316 between roll 318 and the carrier apparatus 308.

As shown in FIG. 5E, the chassis 102 may be combined with the first and second belt laminates 406, 408 such that the third graphics G3 and the first graphics G1 are aligned to form a contiguous design. In particular, the each chassis 102 may be positioned to align the third graphics G3a, G3b with the first portion of the first graphic G1 on the first belt laminate 406 and the second portion of the first graphic G1 on the second belt laminate 408 to form a contiguous design.

With continued reference to FIGS. 4 and 5E, a continuous length of absorbent articles 400 are defined by multiple discrete chassis 102 spaced from each other along the machine direction MD and connected with each other by the second belt laminate 408 and the first belt laminate 406. As shown in FIG. 4, the continuous length of absorbent articles 400 advances from the nip 316 to a folding apparatus 332. At the folding apparatus 332, each chassis 102 is folded in the cross direction CD parallel to or along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt laminate 408 extending between each chassis 102 in a facing relationship with the wearer facing surface 312 of the first belt laminate 406 extending between each chassis 102. As shown in FIGS. 4 and 5F, the folded discrete chassis 102 connected with the first and second belt laminates 406, 408 are advanced from the folding apparatus 332 to a bonder apparatus 334. The bonder apparatus 334 operates to bond an overlap area 362, thus creating discrete bonds 336a, 336b. The overlap area 362 includes a portion of the second belt laminate 408 extending between each chassis 102 and a portion of the first belt laminate 406 extending between each chassis 102.

As shown in FIGS. 4 and 5G, the continuous length of absorbent articles 400 are advanced from the bonder 334 to a cutting apparatus 338 where the first belt laminate 406 and the second belt laminate 408 are cut along the cross direction CD between adjacent bonds 336a, 336b to create discrete absorbent articles 100. As such, bond 336a may correspond with and form a first side seam 178 on an absorbent article 100, and the bond 336b may correspond with and form a second side seam 180 on a subsequently advancing absorbent article. As shown in FIG. 5G, the first belt laminate 406 and the second belt laminate 408 are cut into discrete pieces to form the front and back elastic belts 106, 108, each having a pitch length, PL, extending along the machine direction. As mentioned above, the second graphic defines a maximum length GL in the machine direction MD. In some embodiments, the second graphic G2 extends a length GL in the machine direction that is equal to or less than about 50% of the pitch length PL of the front and back elastic belts 106, 108. And although the first graphics G1a, G1b, G1c, G1d extend in the machine direction for less than 100% of the pitch length PL, it is to be appreciated that the first graphic G1 may be printed so as to extend in the machine direction 100% of the pitch length PL of the belts 106, 108.

It to be appreciated that the converting apparatus 300 may control the relative placement of first elastic belt 106, second elastic belt 108, and/or chassis 102 during the assembly process. For example, in some configurations, the relative placement of first elastic belt 106, second elastic belt 108, and/or chassis 102 may be controlled to align the graphics G1, G2, G3 in a desired manner. For example, the converting apparatus may include a controller adapted to change the machine direction speeds and/or cross direction positions of advancing elastic laminates and/or chassis. Such changes machine direction speeds and/or cross direction positions may be based on the detection of, for example, registration features. In turn, the changes in machine direction speeds and/or cross direction positions may alter the relative alignment of the graphics G1, G2, G3.

Figure 8:
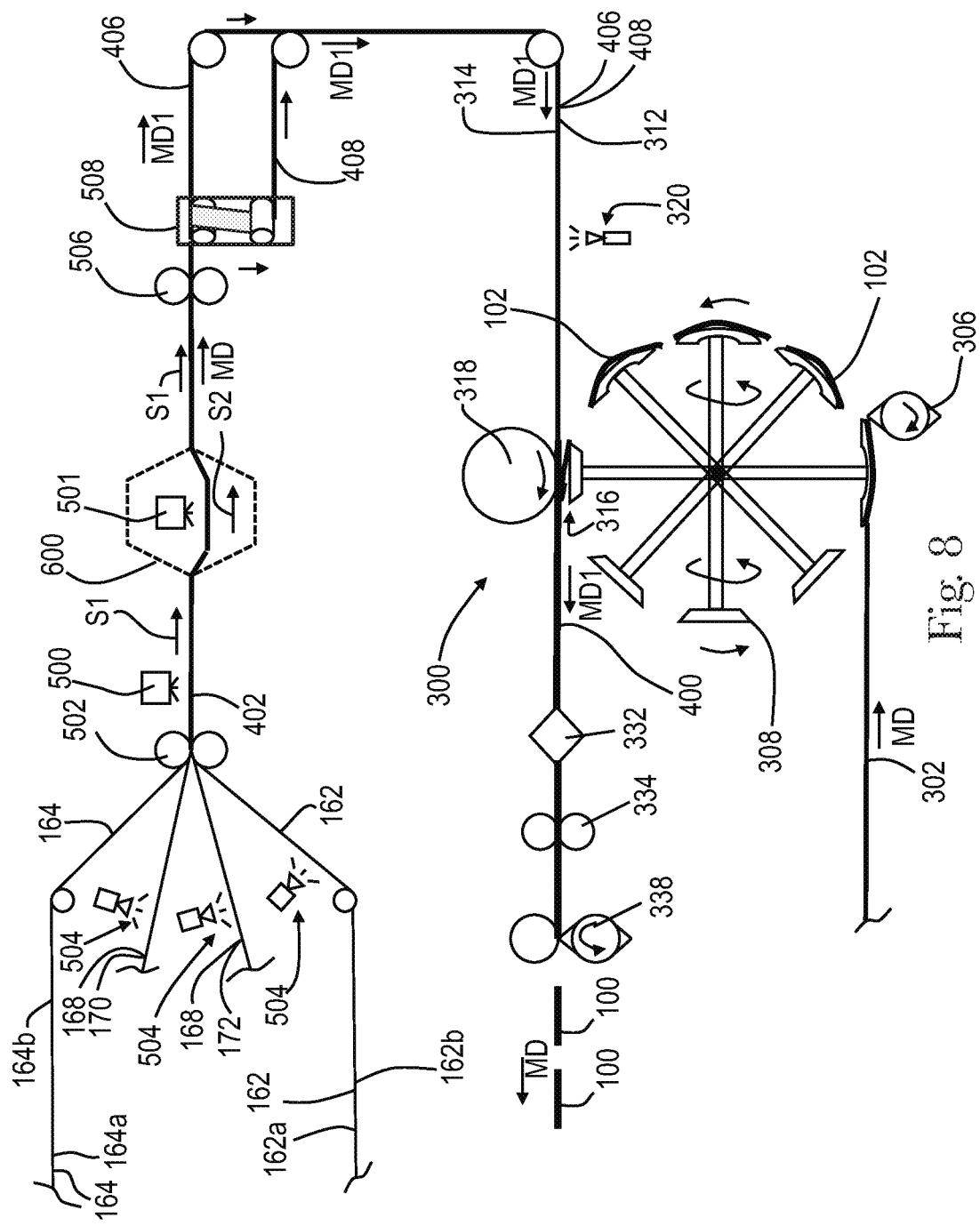
FIG. 8 is a schematic side view of a second embodiment of converting apparatus adapted to manufacture pre-fastened, pant diapers.

Although the above description describes the printing first and second graphics G1, G2 on substrates, such as outer belt substrate 162, before assembly of the belt material 402, it is to be appreciated that the printing process may also occur in other areas of the assembly process. For example, as shown in FIG. 8, the diaper assembly apparatus 300 such as described above with reference to FIG. 4 may be configured to print the first graphics G1 and/or second graphics G2 on the belt material 402 downstream of nip rolls 502 and before being slit into first and second belt substrates 406, 408. In FIG. 8, the belt material 402 advances in the machine direction at a first speed S1 from the nip rolls 502 and past the first printing station 500 that prints the first graphic G1 having a relatively low print resolution on the belt material 402. From the printing station 500, the belt material 402 advances through an accumulator apparatus 600 that decelerates a portion of the belt material 402 to a second speed S2 less than first speed S1. While at the second speed S2, the second printing station 501 prints the second graphic G2 having a relatively high print resolution on the belt material 402. Once the second graphic G2 is printed, the belt material 402 is accelerated back to the first speed S1 and exits the accumulator apparatus 600 to the cutter 506.

Figure 9:
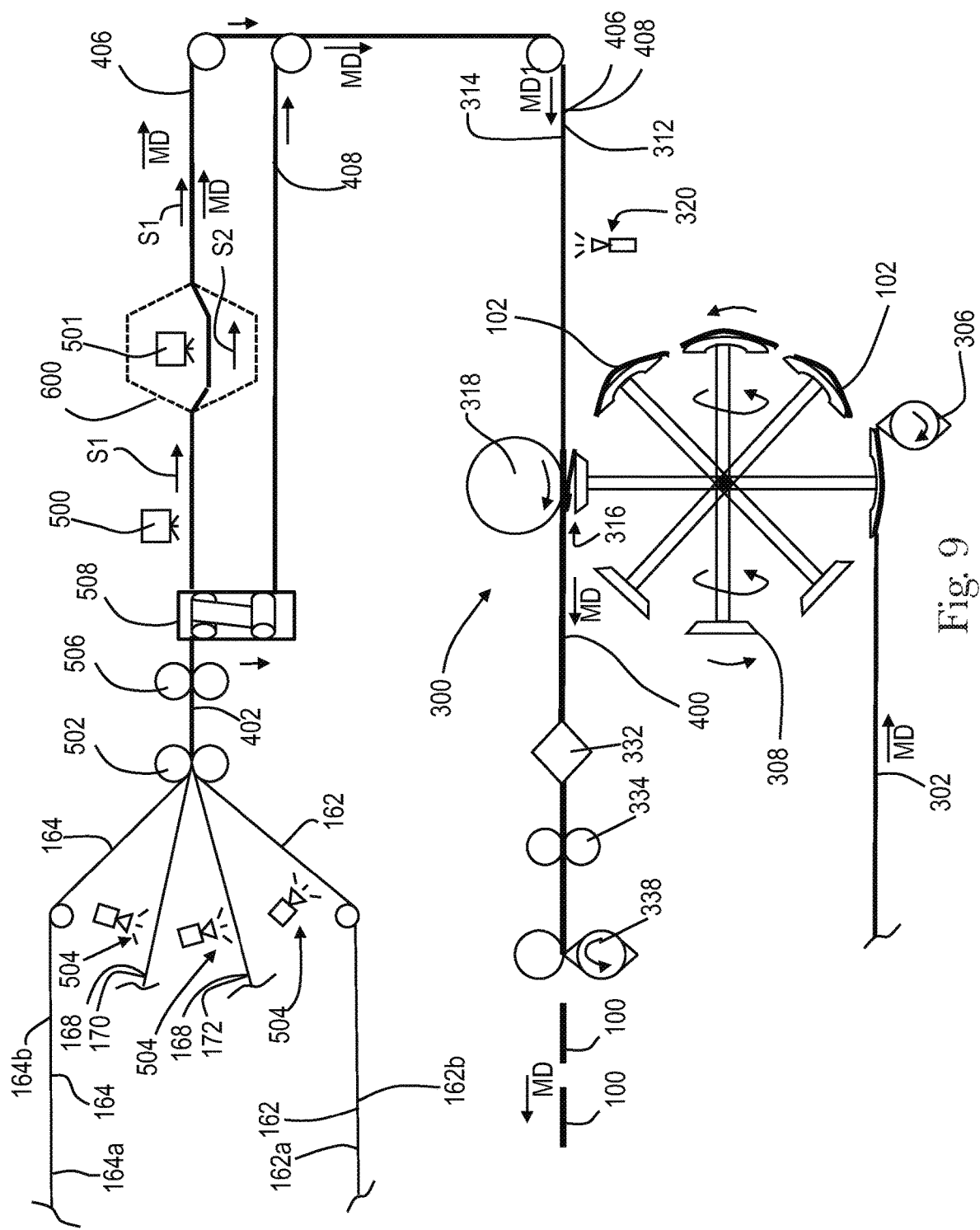
FIG. 9 is a schematic side view of a third embodiment of a converting apparatus adapted to manufacture pre-fastened, pant diapers.

In another example, as shown in FIG. 9, the diaper assembly apparatus 300 such as described above with reference to FIG. 4 may be configured to print the first graphics G1 and/or second graphics G2 on the first and/or second belt substrates 406, 408 downstream of the cutter 506 and before being combined with chassis 102. In the example shown in FIG. 9, the first belt substrate 406 advances in the machine direction at a first speed S1 from the cutter 506 and past the first printing station 500 that prints the first graphic G1 having a relatively low print resolution on the first belt substrate 406. From the printing station 500, the first belt substrate 406 advances through an accumulator apparatus 600 that decelerates a portion of the first belt substrate 406 to a second speed S2 less than first speed S1. While at the second speed S2, the second printing station 501 prints the second graphic G2 having a relatively high print resolution on the first belt substrate 406. Once the second graphic G2 is printed, the first belt substrate 406 is accelerated back to the first speed S1 and exits the accumulator apparatus 600 and is combined with the chassis 102. It is to be appreciated that the apparatus shown in FIG. 9 could also be modified to print first and/or second graphics G1, G2 on the second belt substrate 408 in addition to or as opposed to the first belt substrate 408.

It is to be appreciated that the processes and apparatuses herein may be configured to manufacture various types of diaper pants having graphics G1, G2 such as discussed above. In some embodiments, the diaper pants 100 may include a chassis 102 and elastic belts 106, 108 configured in different ways other than as depicted in FIGS. 1A-2B. For example, FIGS. 10A-11 show a diaper pant 100 having many of the same components as described above with reference to FIGS. 1A-2B, except the outer layer 162 of the elastic belts 106, 108 is configured as a contiguous outer cover 161 that extends through the first waist region 116, crotch region 119, and second waist region 118. Thus, as shown in FIG. 11, the outer cover 161 also includes a first waist end region 116, a crotch region 119, and an opposing second waist end region 118. The outer cover 161 also includes a garment facing surface 162b and an opposing wearer facing surface 162a. As such, elastic members 168 of the elastic belts 106, 108 may be connected with the wearer facing surface 162a of the outer cover 161. And the chassis 102 may be positioned on the wearer facing surface 162a of the outer cover 161. As such, the backsheet 136 may include a portion of the outer cover 161. In addition, the outer cover 161 may include a first longitudinal side edge 128a and a second longitudinal side edge 130a that are positioned laterally outboard the first longitudinal side edge 128 of the chassis 102 and second longitudinal side edge 130 of the chassis 102, respectively, as shown in FIG. 11. As shown in FIGS. 10A and 11, the first longitudinal side edge 128a may define the perimeter 112a of one leg opening 112, and the second longitudinal side edge 130a may define the perimeter 112b of the other leg opening 112. It is to be appreciated also that the first longitudinal side edge 128a and a second longitudinal side edge 130a may aligned with or positioned laterally inboard of the first longitudinal side edge 128 of the chassis 102 and second longitudinal side edge 130 of the chassis 102, respectively. As such, in some embodiments, the perimeter 112a of one leg opening 112 may be defined by portions of the first longitudinal edges 128, 128a, and the perimeter 112b of the other leg opening may be defined by portions of the second longitudinal edges 130, 130a.

Figure 10B:
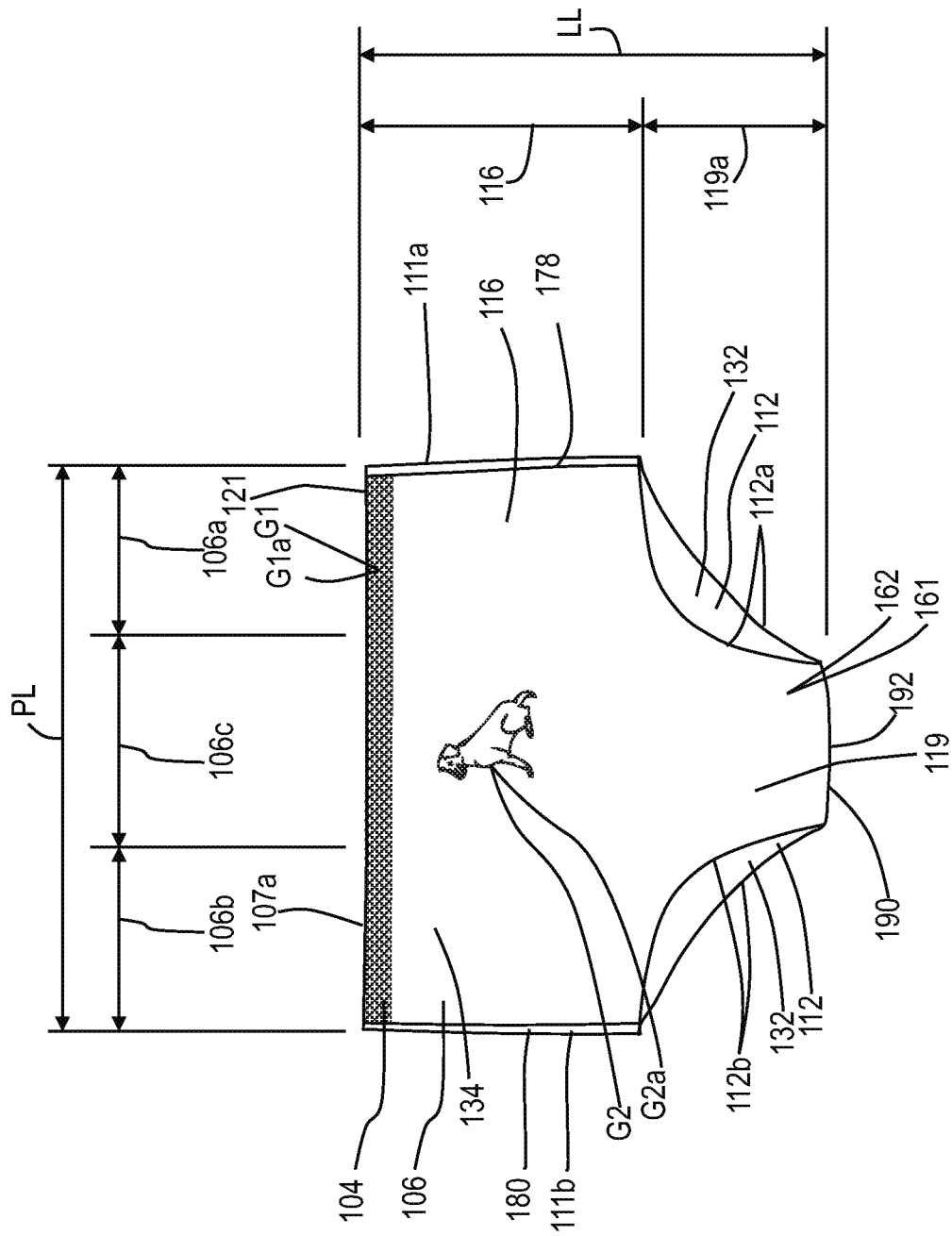
FIG. 10B is a front plan view of the diaper pant of FIG. 10A.
Figure 11:
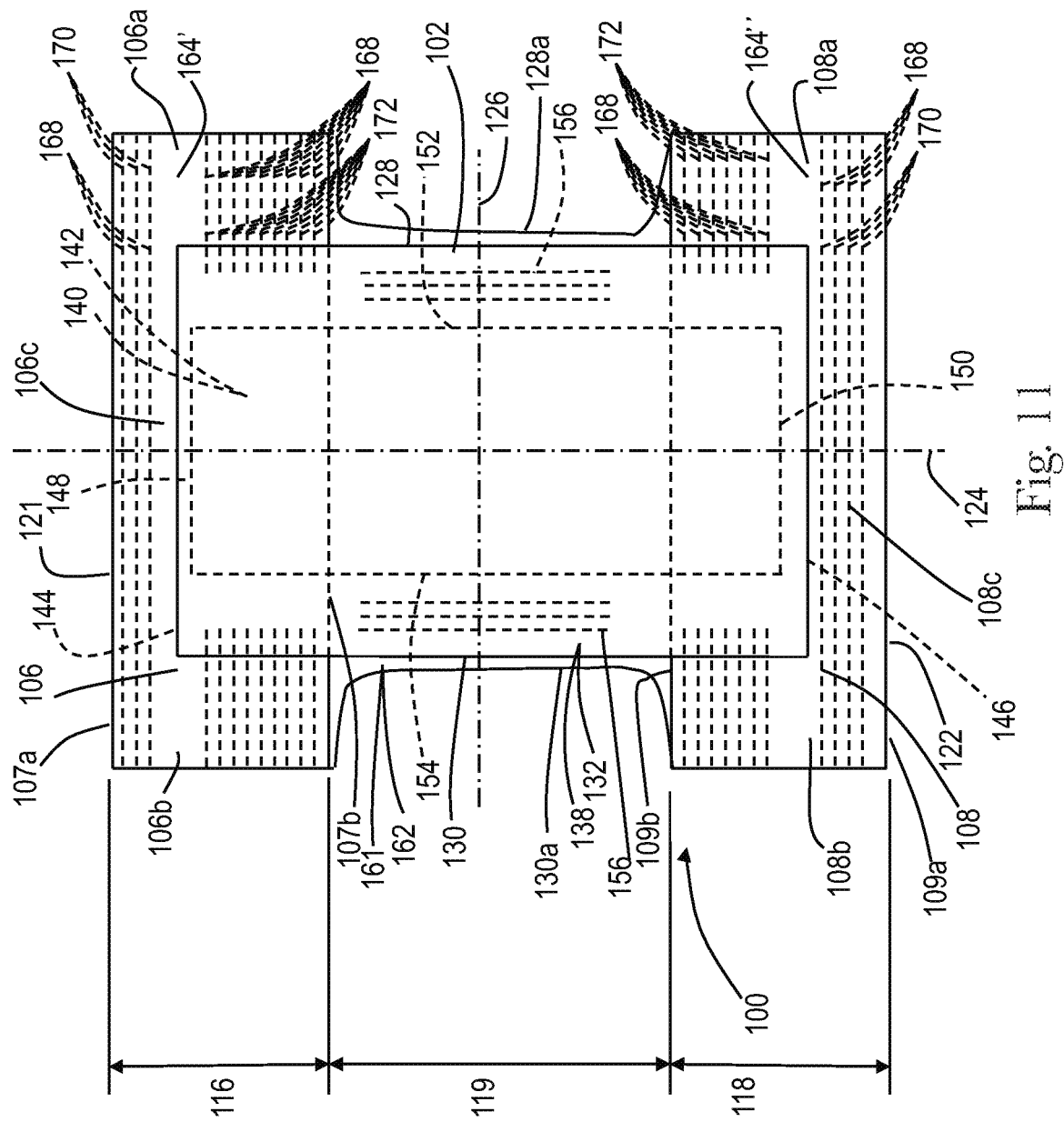
FIG. 11 is a partially cut away plan view of the diaper pant shown in FIGS. 10A-10C in a flat, uncontracted state.

FIG. 10B shows a front plan view of a diaper pant 100 in a laid flat condition illustrating various regions of the diaper pant 100. And 10C shows a rear plan view of the diaper pant 100 in a laid flat condition illustrating various regions of the diaper pant 100. As discussed above, the diaper pant 100 defines include an inner, body facing surface 132, and an outer, garment facing surface 134. The diaper pant 100 also includes a crotch end 190 that is defined by a lateral fold line 192 in the crotch region 119. As such, the lateral fold line 192 divides the crotch region into a first crotch region 119a and a second crotch region 119b.

The diaper pant 100 is shown in FIGS. 10A-10C as having a first elastic belt 106, and a second elastic belt 108.

The first belt 106 has a first end region 106a, an opposing second end region 106b, and a central region 106c. And the second belt 108 has a first end region 108a, an opposing second end region 108b, and a central region 108c. The first end regions 106a, 108a are connected together at a first side seam 178, and the second end regions are 106b, 108b are connected together at a second side seam 180. As shown in FIGS. 10B and 10C, the distance between the first longitudinal edge 111a and the second longitudinal edge 111b defines the pitch length, PL, of the first elastic belt 106, and the distance between the first longitudinal edge 113a and the second longitudinal edge 113b defines the pitch length, PL, of the second elastic belt 108.

The first end region 106a the first belt 106 may extend approximately 20% to 40% of the pitch length PL of the diaper pant 100 in an assembled, laid-flat, relaxed condition, and the first end region 108a the second belt 108 may extend approximately 20% to 40% of the pitch length PL of the diaper pant 100 in an assembled, laid-flat, relaxed condition. The second end region 106b the first belt 106 may extend approximately 20% to 40% of the pitch length PL of the diaper pant 100 in an assembled, laid-flat, relaxed condition, and the second end region 108b the second belt 108 may extend approximately 20% to 40% of the pitch length of the diaper pant 100 in an assembled, laid-flat, relaxed condition. The central region 106c the first belt 106 may extend approximately 20% to 60% of the pitch length PL of the diaper pant 100 in an assembled, laid-flat, relaxed condition, and the central region 108c the second belt 108 may extend approximately 20% to 60% of the pitch length PL of the diaper pant 100 in an assembled, laid-flat, relaxed condition.

The diaper pant 100 in FIGS. 10B and 10C is also shown as having a longitudinal length LL that is defined by the distance between the first waist edge 121 and the crotch end 190 (or the lateral fold line 192), or if longer, the distance from the second waist edge 122 to the crotch end 190 (or the lateral fold line 192). The longitudinal length LL may be measured along the longitudinal centerline 124 of the diaper pant 100. As shown in FIGS. 10B-10C, the first waist region 116 extends a distance generally in the longitudinal direction from the waist edge 121 along the side seams 178, 180 to the leg openings 112, and the second waist region 118 extends a distance generally in the longitudinal direction from the waist edge 122 along the side seams 178, 180 to the leg openings 112. Hence, a first crotch region 119a extends a distance from the crotch end 190 to the first waist region 116, and a second crotch region 119b extends a distance from the crotch end 190 to the second waist region 118. In some embodiments, the first waist region 116 and/or the second waist region 118 may extend about two-thirds the longitudinal length LL of the assembled diaper pant 100. In addition, the first crotch region 119a and/or the second crotch region 119b may extend about one-third the longitudinal length LL of the assembled diaper pant 100.

The diaper pant 100 shown in FIGS. 10A-10C also includes first graphics G1 and second graphics G2 on the first elastic belt 106 and the second elastic belt 108. The first graphics G1 are depicted in the form of a printed stripe G1a extending along the front elastic belts 106 between the first longitudinal edge 111a and the second longitudinal edge 111b. The first graphics G1 are also depicted in the form of a printed stripe G1b extending along the back elastic belts 108 between the first longitudinal edge 113a and the second longitudinal edge 113b. The second graphics G2 are depicted in the form of animals G2a, G2b positioned in the central regions 106c, 108c of the front and back elastic belts 106, 108, respectively. As discussed in more detail below, the first graphics G1 and the second graphics G2 may be printed during the diaper assembly process such that the second graphics G2 include a higher print resolution than the first graphics G1. It is to be appreciated that all graphics discussed herein may be in various different forms, shapes, and/or sizes than those depicted herein.

Figure 12:
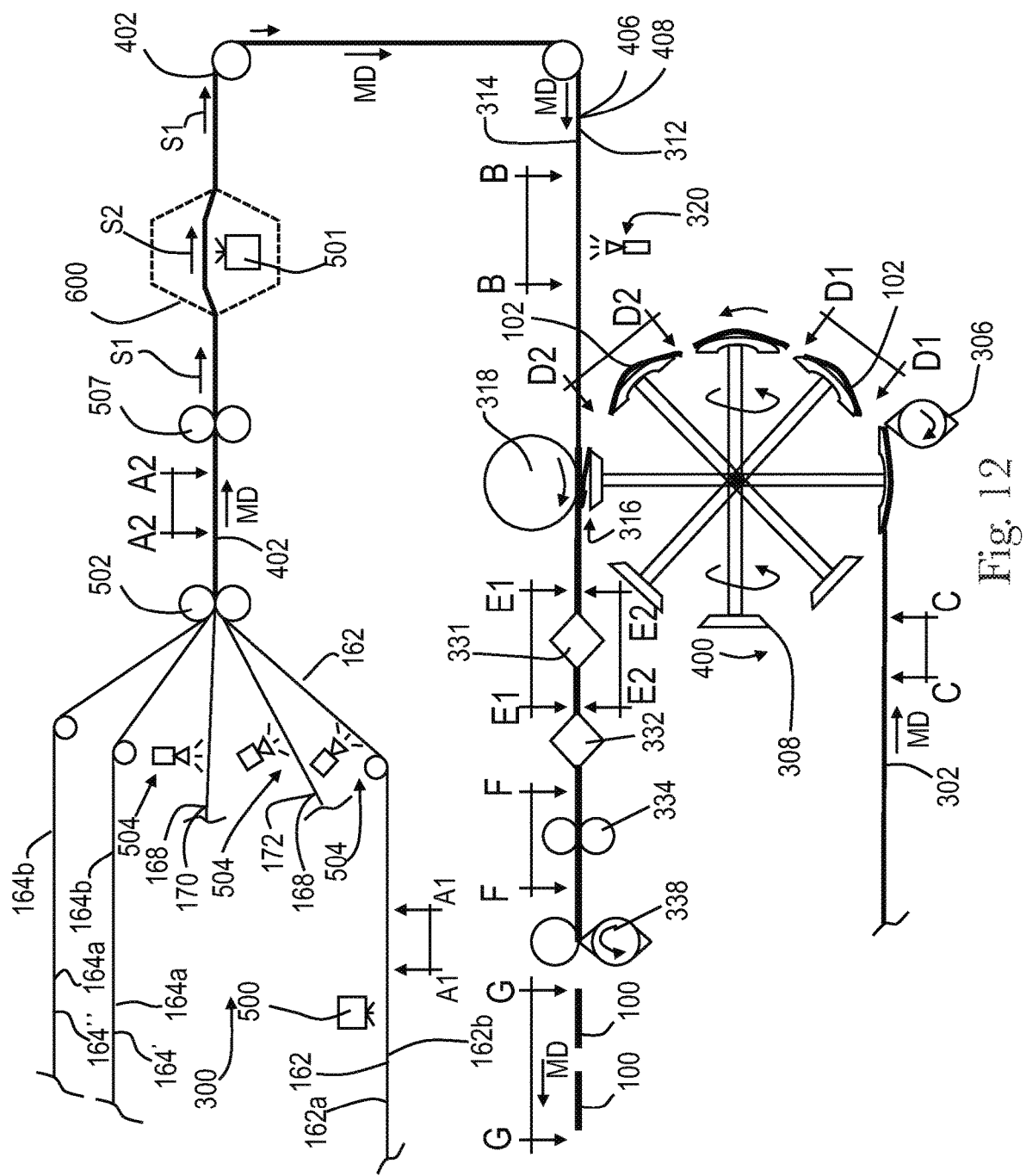
FIG. 12 is a schematic side view of a converting apparatus adapted to manufacture pre-fastened, pant diapers.

As discussed above, during the manufacture of absorbent articles with graphics, such as shown in FIGS. 10A-11, localized speed variances may be imparted to the advancing substrates to achieve the different print resolutions. FIG. 12 shows a converting apparatus 300 configured to assemble diaper pants such as shown in FIGS. 10A-11. As shown in FIG. 12, a first continuous substrate layer in the form of a continuous length of outer layer belt substrate 162 is combined with first and second separate continuous lengths of inner layer belt substrates 164', 164" and elastics 168 form a continuous elastic laminate 402. The outer layer belt substrate 162 also defines the outer cover 161 discussed above with reference to FIGS. 10A-11. With reference to FIGS. 12, 13A1, and 13A2, continuous lengths of outer layer belt substrate 162, first and second inner layers of belt substrate 164', 164", outer elastic strands 170 and inner elastic strands 172 are advanced in a machine direction MD and combined at nip rolls 502 to form the continuous elastic laminate 402.

Before entering the nip rolls 502, the outer layer belt substrate 162 and/or the first and second inner belt substrates 164', 164" may be printed with graphics having a first print resolution as discussed above. As shown in FIGS. 12, 13A1, and 13A2, the outer belt substrate 162 includes first surface 162a and an opposing second surface 162b, and defines a width W in the cross direction between opposing longitudinal edges 163a, 163b. And the outer belt material 162 may advance in the machine direction at a first speed S1 past a first printing station 500 that prints a first graphic G1 on the first surface 162a of the outer belt material 162. The first graphic G1 includes a first print resolution. From the printing station 500, the outer layer belt substrate 162 advances to the nip rolls 502 and is combined with the first and second inner layer belt substrates 164', 164" and elastics 168. The first inner belt substrate 164' includes first surface 164a and an opposing second surface 164b, and defines a width W1 in the cross direction CD between opposing first and second longitudinal edges 165a, 165b. And the second inner belt substrate 164" includes first surface 164a and an opposing second surface 164b, and defines a width W2 in the cross direction CD between opposing first and second longitudinal edges 165a, 165b. As shown in FIG. 13A2, the width W of the outer belt substrate 162 may be greater than the widths W1, W2 of the inner belt substrates 164', 164". And the width W of the outer belt substrate 162 may also define the width W of the elastic laminate 402.

With continued reference to FIG. 12, before entering the nip rolls 502, the outer elastic strands 170 and inner elastic strands 172 are stretched in the machine direction MD. In addition, adhesive 504 may be applied to the elastic strands 170, 172 as well as either or both of the continuous lengths of outer layer belt substrate 162 and inner layer belt substrates 164', 164" before entering nip rolls 502. As such, the elastic strands 168 are bonded between the first surface 162a of the outer layer belt substrate 162 and the first surfaces 164a of inner layer belt substrates 164', 164" at the nip rolls 502. Further, adhesive 504 may be applied intermittently along the lengths of the inner elastic strands 172 and/or intermittently along the length of either or both of the continuous lengths of outer layer belt substrate 162 and inner layer belt substrates 164', 164" before entering nip rolls 502. As previously discussed, the inner elastic strands 172 may be intermittently bonded to either or both of the continuous lengths of outer layer belt substrate 162 and inner layer belt substrates 164', 164" along the machine direction MD.

As shown in FIGS. 12 and 13A2, the continuous elastic laminate 402 includes a first elastic belt laminate 406 and a second elastic belt laminate 408. More particularly, the combination of the outer layer belt substrate 162, the first inner layer of belt substrate 164', and elastic strands 168 defines the first belt laminate 406. And the combination of the outer layer belt substrate 162, the second inner layer of belt substrate 164", and elastic strands 168 defines the second belt laminate 408. The first belt laminate 406 includes an outer longitudinal edge 163a and an inner longitudinal edge 107b that may define a substantially constant width, W1, in the cross direction CD. The inner longitudinal edge 107b may be defined by the second longitudinal edge 165b of the first inner belt substrate 164'. The second belt laminate 408 includes an outer longitudinal edge 163b and an inner longitudinal edge 109b that may define a substantially constant width, W2, in the cross direction CD. The inner longitudinal edge 109b may be defined by the second longitudinal edge 165b of the second inner belt substrate 164". In some configurations, W2 equal to W1. It is also to be appreciated that in some configurations, W1 may be less than or greater than W2. The first belt laminate 406 is separated in the cross direction from the second belt laminate 408 to define a gap between the inner longitudinal edge 107b of the first belt laminate 406 and the inner longitudinal edge 109b of the second belt laminate 408.

Figure 13B:
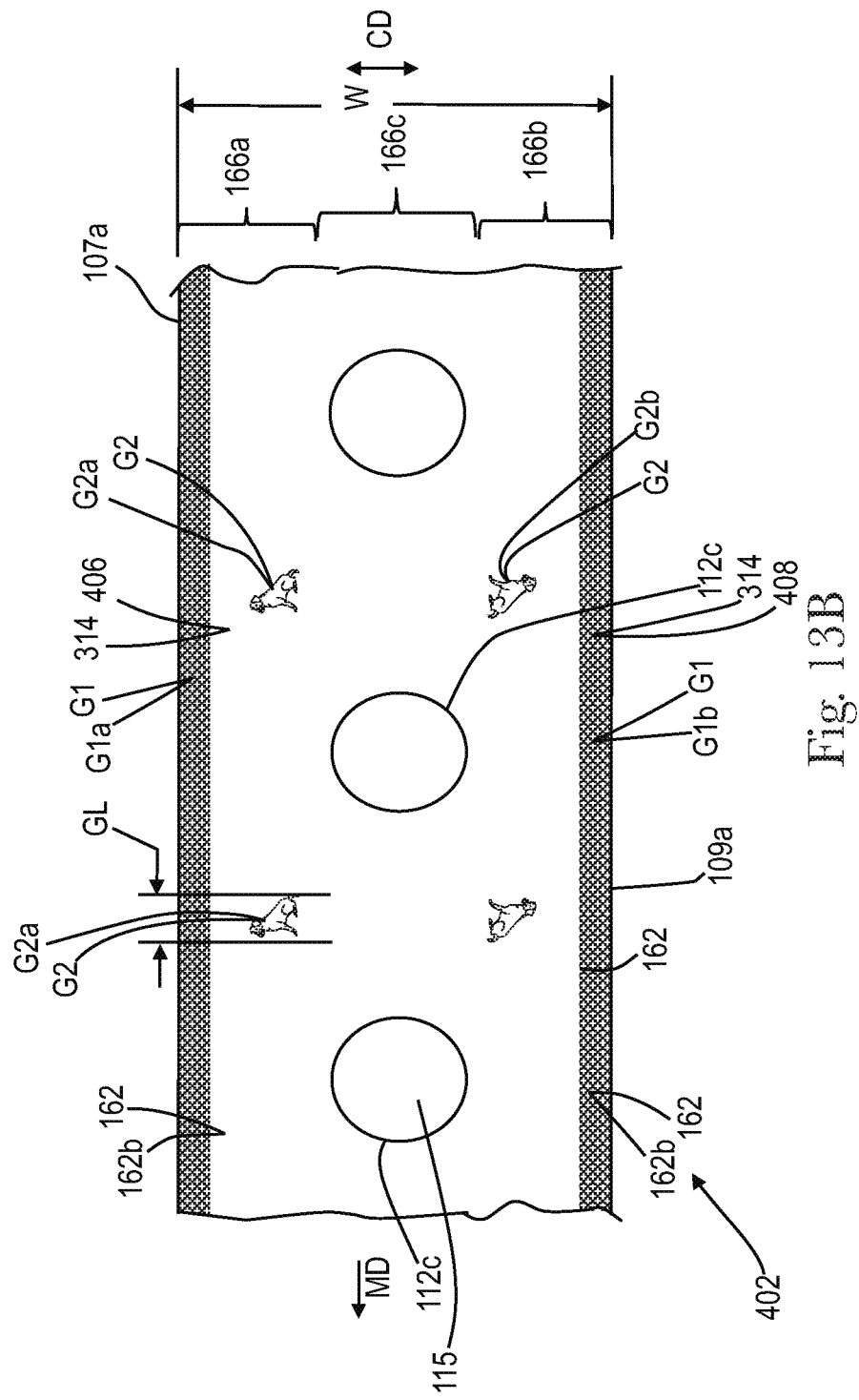
FIG. 13B is a view of continuous lengths of advancing first and second elastic belt laminates from FIG. 12 taken along line B-B.

With continued reference to FIG. 12, from the nip rolls 502 the continuous elastic laminate 402 advances in the machine direction MD to a cutter 507 that removes material from a central region of the continuous elastic laminate 402 to form holes 115 defined by perimeter edges 112c, such as shown in FIG. 13B. The holes 115 are discrete and may be spaced apart from each other along the machine direction MD. The perimeter edges 112c may define all or portions of the perimeters 112a, 112b of the leg openings 112 mentioned above and shown in FIG. 10A. It is to be appreciated that the cutter 507 may be configured to remove material from only the outer layer belt substrate 162. In some configurations, the cutter 507 may be configured to remove material from the outer belt substrate 162 as well as the first inner layer belt substrate 164' and/or second inner layer belt substrate 164". The cutter 507 may also be configured as a perforator that perforates the belt material with a line of weakness and wherein the belt material is separated along the line of weakness in a later step. It is also to be appreciated that the cutter 507 may be configured to form holes 115 in the continuous elastic laminate 402 before or after the continuous elastic laminate 402 is combined with the chassis 102.

With continued reference to FIGS. 12 and 13B, the elastic laminate 402 advances in the machine direction from the cutter 507 at a first speed S1 through an accumulator apparatus 600 that decelerates a portion of the belt material 402 to a second speed S2 less than first speed S1. While at the second speed S2, the second printing station 501 prints the second graphic G2 having a relatively high print resolution on the second surface 162b of the portion 162c of the outer layer belt material 162. The second graphic G2 has a second print resolution. As shown in FIG. 13B, the second graphic may also extend a maximum length GL in the machine direction MD. Once the second graphic G2 is printed, the outer layer belt material 162 is accelerated back to the first speed S1 and exits the accumulator apparatus 600. Once the second graphic G2 is printed, the belt material 402 is accelerated back to the first speed S1 and exits the accumulator apparatus 600. As discussed above, it is to be appreciated that the accumulator apparatus 660 may be configured in various ways, such as for example, as discussed herein with reference to FIGS. 6 and 7.

It is to be appreciated that the first and second printing stations 500, 501 may positioned in various different locations relative to the process operations show in FIG. 12. For example, the first and/or second printing stations 500, 501 may be positioned upstream or downstream of the nip rolls 502, the cutter 507, and/or the nip 316. In addition, the first printing station 500 may be positioned downstream of the second printing station 501 such that first graphics G1 are printed subsequent to the second graphics G2. With further reference to FIGS. 12, 13A1, and 13B, although the first graphics G1 are printed on the first surface 162a of the outer layer belt substrate 162, the first graphics G1 may be visible through the second surface 162b. It is also to be appreciated that the first and/or second printing stations 500, 501, and/or additional printing stations, may be arranged to print graphics on either or both the first and second surfaces 162a, 162b of the outer belt substrate 162. It is also to be appreciated that graphics may be printed on either or both the first and second surfaces 164a, 164b of the first and second inner belt substrates 164', 164". It is also to be appreciated that the printing stations 500, 501 herein may be configured in various ways and may include various types of printing accessories as discussed above. For example, in some embodiments, the printing stations 500, 501 may include a printer in the form of an ink-jet printer. It is also to be appreciated that more than one substrate may be printed, and as such, the substrates may have different properties, such as basis weights, fiber characteristics, and/or surface coatings. In addition, different types of printing may be applied to the substrates. For example, one substrate may be printed with flexography and/or gravure printing processes, while another substrate may be printed with inkjet printing processes. It is to be appreciated that the printing may be done during the assembly process and/or may done separate to the assembly process, such as for example, printing the substrates off line wherein the printed substrates may be stored until needed for production. In some instances, customized graphic printing processes may also be utilized, for example such as disclosed in U.S. Pat. No. 8,776,683.

As discussed with reference to FIGS. 12-13B, the first graphics G1 may be printed on the substrate 162 while advancing at a first speed S1, and the second graphics G2 may be printed on a portion 162c of the substrate 162 while advancing at a second speed S2, wherein the second speed S2 is less than the first speed S1. As discussed above, it is to be appreciated that system may be configured with various relative differences between the first speed and second speeds. For example, in some configurations, the second speed S2 is from about 25% to about 50% of the first speed S1. In some configurations, the second speed S2 is about 25% of the first speed S1. Also as mentioned above, the second print resolution of the second graphics G2 is greater than the first print resolution of the first graphics G1, because the first graphics G1 are printed while the substrate 162 is advancing at relatively high speed S1 and the second graphics G2 are printed while the portion 162c of the substrate 162 is advancing at a relatively low speed S2. Thus, it is to be appreciated that system may be configured with various relative differences between the first and second print resolutions. For example, in some configurations, the second graphic G2 may have a second print resolution that is equal to or greater than about 400% of the first print resolution of the first graphic G1. In some configurations, the second graphic G2 may have a second print resolution that is equal to or greater than about 200% of the first print resolution of the first graphic G1. In some configurations, the second graphic G2 may have a second print resolution that is from about 200% to about 500% of the first print resolution of the first graphic G1. In some configurations, the first print resolution is from about 20% to about 50% of the second print resolution. In some configurations, the first print resolution is from about 25% to about 75% of the second print resolution. In some configurations, the first print resolution may be from about 80 dots per inch (DPI) to about 200 dots per inch (DPI); and the second print resolution may be equal to or greater than about 400 dots per inch (DPI). In one example, a print station capable of printing at a 400 dots per inch (DPI) resolution on a substrate advancing at 1.5 m/s may print at a 200 dots per inch (DPI) resolution on a substrate advancing at 3 m/s, and may print at a 100 dots per inch (DPI) resolution on a substrate advancing at 6 m/s.

It is to also to be appreciated that the graphics G1, G2 may be printed to have differing designs from each other along the machine direction MD and/or cross direction CD. Also shown in FIG. 13B, the outer belt substrate 162, and thus the elastic laminate 402, may include first and second outer longitudinal regions 166a, 166b separated in the cross direction CD by a central region 166c. And either or both the graphics G1a, G2a may be positioned entirely within the first outer longitudinal region 166a, and either or both the graphics G1b, G2b may be positioned entirely within the second outer longitudinal region 166b. In some embodiments, either or both the graphics G1, G2 may be positioned entirely within the central region 166c of the elastic laminate 402. It is to be appreciated the widths of the regions 166a, 166b, 166c may vary. For example, in some embodiments, the central region 166c may be about 33% of the width W of the elastic laminate 402. In some embodiments, the first and second outer longitudinal regions 166a, 166b and/or the central region may each be about ⅓ of the width W of the elastic laminate 402.

As discussed above with reference to FIGS. 4, 5C, 5D1, and 5D2, and as shown in FIG. 12, a continuous length of chassis assemblies 302 are advanced in a machine direction MD to a carrier apparatus 308 and are cut into discrete chassis 102 with knife roll 306, while advancing in the orientation shown in FIG. 5D1. After the discrete absorbent chassis 102 are cut by the knife roll 306, the carrier apparatus 308 rotates and advances the discrete chassis 102 in the machine direction MD in the orientation shown in FIG. 5D1. The carrier apparatus 308 also rotates while at the same time changing the orientation of the advancing chassis 102. In changing the chassis orientation, the carrier apparatus 308 may turn each chassis 102 such that the lateral axis 126 of the chassis 102 is parallel or generally parallel with the machine direction MD, such as shown in FIG. 5D2.

As shown in FIGS. 12, 13E1, and 13E2, the chassis 102 are transferred from the carrier apparatus 308 to a nip 316 between the carrier apparatus 308 and a roll 318 where the chassis 102 is combined with the continuous elastic laminate 402. The chassis 102 may be spaced apart from each other along the machine direction MD on the continuous elastic laminate 402, wherein at least one hole 115 is positioned between two consecutive chassis 102. The continuous elastic laminate 402 includes a wearer facing surface 312 and an opposing garment facing surface 314. As such, the second surface 162b of the outer layer belt substrate 162 may define the garment facing surface 314. And the first surface 162a of the outer layer belt substrate 162 and the second surfaces 164b of the inner layer belt substrates 164', 164" may define the wearer facing surface 312. The wearer facing surface 312 of the continuous elastic laminate 402 may be combined with the garment facing surface 134 of the chassis 102. As shown in FIG. 12, adhesive 320 may be intermittently applied to the wearer facing surface 312 of the continuous elastic laminate 402 before combining with the discrete chassis 102 at the nip 316 between roll 318 and the carrier apparatus 308.

With continued reference to FIGS. 12, 13E1, and 13E2, a continuous length of absorbent articles 400 are defined by multiple discrete chassis 102 spaced from each other along the machine direction MD and connected with each other by the continuous elastic laminate 402. As shown in FIG. 12, the continuous length of absorbent articles 400 advances from the nip 316 to a folding apparatus 332. At the folding apparatus 332, the continuous elastic laminate 402 and each chassis 102 are folded in the cross direction CD parallel to or along a lateral axis 126 to place the first waist region 116, and specifically, the inner, body facing surface 132 into a facing, surface to surface orientation with the inner, body surface 132 of the second waist region 118. The folding operation creates the lateral fold line 192 that defines the crotch end 190 discussed above with reference to FIGS. 10B and 10C. The folding of the chassis also positions the wearer facing surface 312 of the second belt laminate 408 extending between each chassis 102 in a facing relationship with the wearer facing surface 312 of the first belt laminate 406 extending between each chassis 102.

As shown in FIGS. 12 and 13F, the folded continuous length of absorbent articles 400 are advanced from the folding apparatus 332 to a bonder apparatus 334. The bonder apparatus 334 operates to bond an overlap area 362, thus creating discrete bonds 336a, 336b. The overlap area 362 includes a portion of the second belt laminate 408 extending between each chassis 102 and a portion of the first belt laminate 406 extending between each chassis 102. It is to be appreciated that the bonder apparatus 334 may be configured in various ways to create bonds 336a, 336b in various ways, such as for example with heat, adhesives, pressure, and/or ultrasonics. It is also to be appreciated that in some embodiments, the apparatus 300 may be configured to refastenably bond the overlap area 362, in addition to or as opposed to permanently bonding the overlap area 362. Thus, the discrete bonds 336a, 336b may be configured to be refastenable, such as with hooks and loops.

Referring now to FIGS. 12 and 13G, the continuous length of absorbent articles 400 are advanced from the bonder 334 to a cutting apparatus 338 where the first belt laminate 406 and the second belt laminate 408 are cut along the cross direction CD between adjacent bonds 336a, 336b to create discrete absorbent articles 100. As shown in FIG. 13G, the continuous length of absorbent articles 400 are cut into discrete pieces to form the front and back elastic belts 106, 108, each having a pitch length, PL, extending along the machine direction MD and longitudinal length LL extending in the cross direction CD. As such, bond 336a may correspond with and form a first side seam 178 on an absorbent article 100, and the bond 336b may correspond with and form a second side seam 180 on a subsequently advancing absorbent article. As mentioned above, the second graphic G2 defines a maximum length GL in the machine direction MD. In some embodiments, the second graphics G2a, G2b may extend a length GL in the machine direction that is equal to or less than about 50% of the pitch length PL of the front and back elastic belts 106, 108. And although the first graphics G1*a*, G1*b* extend contiguously in the machine direction for 100% of the pitch length PL, it is to be appreciated that the first graphics G1*a*, G1*b* may be printed so as to extend in the machine direction for less than 100% of the pitch length PL of the belts 106, 108.

It is also to be appreciated that the first graphics G1, second graphics G2, and/or third graphics G3 described herein may be configured to different graphics, standard graphics, custom graphics, and/or personalized graphics. "Different in terms of graphic design" means that graphics are intended to be different when viewed by users or consumers with normal attentions. Thus, two graphics having a graphic difference(s) which are unintentionally caused due to a problem(s) or an error(s) in a manufacture process, for example, are not different from each other in terms of graphic design. "Standard" or "standardized" refers to graphics, products, and/or articles that have the same aesthetic appearance without intending to be different from each other. The term "custom" or "customized" refers to graphics, products, and/or articles that are changed to suit a small demographic, region, purchaser, customer, or the like. Custom graphics may be selected from a set of graphics. For example, custom graphics may include animal depictions selected from groups of animals, such as farm animals, sea creatures, birds, and the like. In other examples, custom graphics may include nursery rhymes and the like. In one scenario, custom products or articles may be created by a purchaser of such products or articles wherein the purchaser selects graphics for the articles or products from a set of graphics offered by a manufacturer of such articles or products. Custom graphics may also include "personalized" graphics, which may be graphics created for a particular purchaser. For example, personalized graphics may include a person's name alone or in combination with a design.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising the steps of:

advancing a first continuous substrate having a first surface and an opposing second surface in a machine direction at a first speed, and defining a width in a cross direction;

inkjet printing a first graphic on the first continuous substrate while the first continuous substrate is advancing at the first speed, the first graphic comprising a first print resolution;

decelerating a portion of the first continuous substrate to a second speed;

inkjet printing a second graphic on the portion of the first continuous substrate while at the second speed, the second graphic comprising a second print resolution, wherein the second print resolution is greater than the first print resolution;

accelerating the portion of the first continuous substrate from the second speed to the first speed;

advancing a second continuous substrate having a first surface and an opposing second surface in the machine direction, and defining a width in the cross direction;

bonding elastic strands in a stretched state between the first surface of the first continuous substrate and the first surface of the second continuous substrate to form a continuous elastic laminate;

cutting the elastic laminate along the machine direction to form a first continuous elastic laminate and a second continuous elastic laminate, wherein the first continuous elastic laminate includes the first graphic and the second graphic;

separating the first continuous elastic laminate in the cross direction from the second continuous elastic laminate;

depositing a plurality of chassis spaced apart from each other along the machine direction onto the first continuous elastic laminate and the second continuous elastic laminate;

folding each chassis along the lateral axis to position the first continuous elastic laminate into a facing relationship with the second continuous elastic laminate; and cutting the first and second continuous elastic laminates into discrete pieces each having a pitch length, PL, extending along the machine direction, wherein the second graphic extends in the machine direction for less than the pitch length.

2. The method of claim 1, wherein the step of cutting the elastic laminate along the machine direction further comprises cutting through the first graphic such that the first continuous elastic laminate includes a first portion of the first graphic and the second continuous elastic laminate includes a second portion of the first graphic.

3. The method of claim 2, wherein each chassis comprises a third graphic, and further comprising the step of positioning each chassis to align the third graphic with the first portion of the first graphic to form a contiguous design.

4. The method of claim 3, further comprising the step of positioning each chassis to align the third graphic with the second portion of the first graphic to form a contiguous design.

5. The method of claim 1, wherein the step of depositing the plurality of chassis further comprise placing the backsheet of each chassis directly onto the second surface of the first continuous substrate.

6. The method of claim 1, wherein the first graphic extends in the machine direction for less than 100% of the pitch length.

7. The method of claim 1, wherein the first print resolution is from about 80 DPI to about 200 DPI.

8. The method of claim 1, wherein the second speed is about 25% of the first speed.

9. The method of claim 1, wherein the first graphic is printed before the second graphic is printed.

10. A method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising the steps of:

advancing a first continuous substrate having a first surface and an opposing second surface in a machine direction at a first speed, and defining a width in a cross direction;

inkjet printing a first graphic on the first continuous substrate while the first continuous substrate is advancing at the first speed, the first graphic comprising a first print resolution;

decelerating a portion of the first continuous substrate to a second speed;

inkjet printing a second graphic on the portion of the first continuous substrate while at the second speed, the second graphic comprising a second print resolution greater than the first print resolution;

accelerating the portion of the first continuous substrate from the second speed to the first speed;

advancing a second continuous substrate having a first surface and an opposing second surface in the machine direction, and defining a width in the cross direction;

bonding elastic strands in a stretched state between the first continuous substrate and the second continuous substrate to form a continuous elastic laminate;

cutting the elastic laminate along the machine direction to form a first continuous elastic laminate and a second continuous elastic laminate;

separating the first continuous elastic laminate in the cross direction from the second continuous elastic laminate;

depositing a plurality of chassis spaced apart from each other along the machine direction onto the first continuous elastic laminate and the second continuous elastic laminate;

folding each chassis along the lateral axis to position the first continuous elastic laminate into a facing relationship with the second continuous elastic laminate; and cutting the first and second continuous elastic laminates into discrete pieces each having a pitch length, PL, extending along the machine direction, wherein the second graphic extends in the machine direction for less than the pitch length.

11. The method of claim 10, wherein the first print resolution is about 25% to about 75% of the second print resolution.

* * * * *